(12) United States Patent
Holy et al.

(10) Patent No.: US 6,653,296 B1
(45) Date of Patent: Nov. 25, 2003

(54) ANTIRETROVIRAL ENANTIOMERIC NUCLEOTIDE ANALOGS

(75) Inventors: Antonin Holy, Horni Pocernice (CZ); Hana Dvorakova, Prague (CZ); Erik Desire Alice De Clercq, Lovenjoel (BE); Jan Marie Rene Balzarini, Heverlee (BE)

(73) Assignees: Institute of Organic Chemistry and Biochemistry of the Academy of Sciences of the Czech Republic (CZ); Rega Stichting v.z.w. (BE)

( * ) Notice: Subject to any disclaimer, the term of this patent is extended or adjusted under 35 U.S.C. 154(b) by 0 days.

(21) Appl. No.: 08/379,551

(22) PCT Filed: Aug. 4, 1993

(86) PCT No.: PCT/US93/07360

§ 371 (c)(1),
(2), (4) Date: Feb. 2, 1995

(87) PCT Pub. No.: WO94/03467

PCT Pub. Date: Feb. 17, 1994

Related U.S. Application Data

(63) Continuation-in-part of application No. 07/925,610, filed on Aug. 5, 1992.

(51) Int. Cl.$^7$ ...................... A61K 31/675; C07F 9/6561
(52) U.S. Cl. ........................... 514/81; 514/84; 514/86; 514/89; 544/118; 544/182; 544/243; 544/244; 546/22; 546/23; 546/24; 546/118; 549/416; 558/179; 558/183; 558/186; 558/188; 558/189; 568/663
(58) Field of Search ................. 544/244, 118; 514/81; 558/179, 183, 186, 188–189

(56) References Cited

U.S. PATENT DOCUMENTS

| | | | |
|---|---|---|---|
| 4,659,825 A | 4/1987 | Holy et al. | 544/244 |
| 4,724,233 A | 2/1988 | De Clercq et al. | 514/81 |
| 4,808,716 A | * 2/1989 | Holy et al. | 544/244 |
| 5,130,427 A | * 7/1992 | Alexander et al. | 544/182 |
| 5,142,051 A | 8/1992 | Holy et al. | 544/244 |
| 5,302,585 A | 4/1994 | Yu et al. | 514/81 |
| 5,466,806 A | 11/1995 | Belleau et al. | |
| 5,476,938 A | * 12/1995 | Vemishetti et al. | 544/243 |
| 5,650,510 A | * 7/1997 | Webb, II et al. | 544/244 |
| 6,057,305 A | * 5/2000 | Holy et al. | 514/81 |

FOREIGN PATENT DOCUMENTS

| | | | |
|---|---|---|---|
| DE | 3906357 | * | 9/1990 |
| EP | 009155 | * | 4/1980 |
| EP | 130126 | * | 1/1985 |
| EP | 253412 | * | 1/1988 |
| EP | 269947 | * | 6/1988 |
| EP | 292244 | * | 11/1988 |
| EP | 322815 | * | 7/1989 |
| EP | 368410 | * | 5/1990 |
| EP | 452935 | * | 10/1991 |
| EP | 481214 | * | 4/1992 |
| GB | 544419 | * | 4/1979 |
| WO | WO 84/04748 | | 12/1984 |
| WO | WO 95/32983 | | 12/1995 |

OTHER PUBLICATIONS

Clayette et al, *Antiviral Chemistry & Chemotherapy*, 2 p 329–336 (1991).*

Sugawara et al, *Agric. Biol. Chem. 50,* p 2261–2271(1986).*

*Organic Chemistry* by Paul Karrer (2nd Ed.) pp 92–102 (1946).*

*Internal Medicine* (4th Ed) by Jay Stein (Editor–in–Chief) p 600–601, 2047 (1994).*

Bronson et al, *Nucleotide Analogs as Antiviral Agents,* ACS Symposium Series 401 (1989), pp 72–87.*

Balzarini et al, *Antimicrobial Agents & Chemotherapy 2,* p 332–338 (1993).*

Schaeffer et al, *J. Med. Chem.* 8 p 502–506 (1965).*

Colla et al, *Eur. J. Med. Chem. 17,* pp 569–576 (1982).*

The Merck Index (Merck & Co, publishers) p. 7870 (1989). (1989).*

Vince et al., "6–Substituted Derivatives of Carbovir: Anti-HIV Activity," Nucls & Nuclt 14(8):1703–1708 (1995).*

Webb et al., "Antiviral phosphonomethoxyalkylpurines and pyrimidines and their preparation.," Chem AB 109:190136p (1988).*

Yang et al., "New Antiretroviral Acyclic Nucleotide Analog: (R)–2'–Me–PMEG ((R)–N(2–phosphonylmethoxypropylguanine)," Antiviral Res 162:131 (1991).*

Yokota et al, "Inhibitory effects of acyclic nucleoside phosphonate analogues on hepatitis B virus DNA synthesis in HB611 cells," Antiviral Chem & Chemo 5(2):57–63 (1994).*

(List continued on next page.)

Primary Examiner—Emily Bernhardt
Assistant Examiner—C Styles
(74) Attorney, Agent, or Firm—Max D. Hensley

(57) ABSTRACT

Resolved enantiomers of the formula (IA) and (IB)

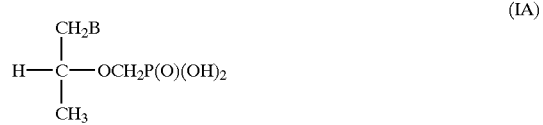

(IA)

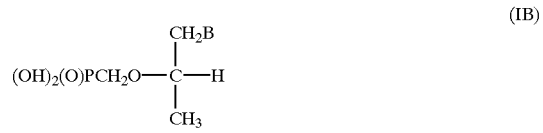

(IB)

wherein B is a purine or pyrimidine base or aza and/or deaza analogs thereof are useful in antiviral pharmaceutical compositions to treat retroviral infections.

40 Claims, No Drawings

OTHER PUBLICATIONS

Anon., Antiviral Agents Bulletin, 8(11):325–326 (1995).*

Dvorakova et al, "Synthesis and Antiviral Activity of Acyclic Nucleoside and Nucleotide Derivatives of 8–Azaadenine," Collect Czech Chem Commun 58:253–255 (1993).

Gilson et al., "A Placebo–Controlled Phase I/II Study of Adefovir Dipivoxil (Bis–Pom PMEA) in Patients with Chronic Hepatitis B Infection," American Association for the Study of Liver Diseases Abstract (Nov. 8–12, 1996).

Greene et al., Protective Groups in Organic Synthesis (2nd Ed.) (John Wiley & Sons), p. 362, 364–367 (1991).

Holy et al, "Acyclic nucleotide analogues: synthesis, antiviral activity and inhibitory effects on some cellular and virus–encoded enzymes in vitro," Antiviral Res 13:295–312 (1990).

Holy et al, "Antiviral Activity of 2–Phosphonomethoxyalkyl Derivatives of N6–Substituted 6–Aminopurines," 8th International Conference on Antiviral Research, Santa Fe, NM 26(3):A231 (1995).

Holy et al., "3'–O–Phosphonylmethyl–9–(S)–(2,3–dihydroxypropyl)adenine novel type of biologically active nucleotide analogue," Nuc Acids Res 14:277–278 (1984).

Holy et al., "Phosphonylmethyl Ethers of Nucleosides and Their Acyclic Analogues," ACS Symposium Series 401:51–71 (1989).

Holy et al., "Synthesis and evaluation of acyclic nucleotide analogs," Chem Ab 111(3):23866m (1989).

Hudlicky, Reductions in Organic Chemistry, pp. 76, 92–96 (1984).

Kim et al, "A new class of acyclic phosphonate nucleotide analogues: phosphonate isosteres of acyclovir and ganciclovir monophosphates as antiviral agents," J Med Chem 34(7):2286–2294 (1991).

Kim et al, "Acyclic Purine Phosphonate Analogues as Antivral Agents. Synthesis and Structure—Activity Relationships," J Med Chem 33:1207–1213 (1990).

Koszalka et al, "Inhibition of HIV– and HBV–Virus Replication By 2,6–Disubstituted Purine 2',3'–Dideoxynucleosides," Poster (4/95).

Martin et al., "Synthesis and antiherpesvirus activity of (S)–1–((3–hydroxy–2–phosphonylmethoxy)propyl.)cytosine (HPMPC) and related nucleotide analogues," Nucls & Nuclt 8:923–926 (1989).

Prisbe et al., "Synthesis and Antiherpes Virus Activity of Phosphate and Phosphonate Derivatives of 9–[1,3–Dihydroxy–2–propoxy)methyl]guanine," J Med Chem 29:671–675 (1986).

Rosenberg et al., "Acyclic nucleotide analogs. IV. Phosphonyl methoxyalkyl and phosphonylalkyl derivatives of adenine," Chem Ab 111(19):174565p (1989).

Stinson, S.C., "Chiral Drugs," C&E News pp. 38–65 (Sep. 27, 1993).

Tsai et al., "Prevention of SIV Infection in Macaques by (R)–9–(2–Phosphonylmethoxypropyl)adenine," Science 270:1197–1199 (Nov. 17, 1995).

Vahlenkamp et al., "(R)–9–(2–Phosphonylmethoxypropyl)–2,6–Diaminopurine Is a Potent Inhibitor of Feline Immunodeficiency Virus Infection," Antimicro Ag & Chemo 39(3):746–749 (1995).

Levy et al., 3rd ed., Chap. 6, pp. 130, 143–146, Virology, 1983.

Balzarini et al, "Activity of the (R)–Enantiomers of (9–2–Phosphonylmethoxypropyl)–Adenine and 9–(2–Phosphonylmethoxypropyl)–2,6–diaminopurine against Human Immunodeficiency Virus in Different Human Cell Systems," Biochem Biophys Res Comm 219:337–341 (1996).

Balzarini et al., Aids Res & Hum Retro, 5:21–28 (1991).

Cohen, John, "New Drug Shows Promise in Monkeys," Science 270:1121–1122 (Nov. 17, 1995).

De Clercq et al, "A novel selective broad–spectrum anti–DNA virus agent," Nature 323:464–467 (1986).

De Clercq et al., "(S)–9–(2,3–dihydroxypropyl)adenine: An Aliphatic Nucleoside Analog with Broad–Spectrum Antiviral Activity," Science 200:563–565 (1978).

De Clercq et al., "Antiviral activity of phosphonylmethoxyalkyl derivatives of purine and pyrimidines," Antiviral Res 8:261–272 (1987).

De Clercq et al., "Efficacy of Phosphonylmethoxyalkyl Derivatives of Adenine in Experimental Herpes Simplex Virus and Vaccinia Virus Infections in Vivo," Antimicro Ag & Chemo 33(2):185–191 (1989).

* cited by examiner

ANTIRETROVIRAL ENANTIOMERIC NUCLEOTIDE ANALOGS

This application is a 371 of PCT/US93/07360 filed Aug. 4, 1993, which is a continuation-in-part of U.S. application Ser. No. 07/925,610 filed Aug. 5, 1992, now U.S. Pat. No. 6,057,305.

FIELD OF THE INVENTION

This invention concerns acyclic nucleotide analogs, their preparation and use. In particular it concerns separate enantiomers of 2-phosphonomethoxypropyl derivatives of purine and pyrimidine bases.

BACKGROUND OF THE INVENTION

There is an urgent need for development of chemotherapeutic agents in the therapy of viral diseases. In particular treatment of diseases caused by retroviruses presents one of the most difficult challenges in human medicine. While a number of antiviral agents which are registered or are currently under study can effectively cure disease, relieve symptoms or substantially prolong the intervals among the recurrences of certain chronic viral infections, such positive outcomes have not yet been achieved in many instances, notably that of AIDS, as an example of retroviral disease. Selectivity of antiviral action, which is an important requirement for novel antiviral agents, has not been achieved.

Most of the compounds which are clinically useful for antiviral chemotherapy are nucleosides, modified in either the purine or pyrimidine base and/or the carbohydrate moiety. Such compounds mainly act in processes related to the synthesis of viral nucleic acids; their action depends on ability to undergo phosphorylation and subsequent transformation to the triphosphates. One problem in administering modified nucleosides is the absence of suitable phosphorylating activity in the host cell and the existence of viral strains lacking virus-specific phosphorylating activity. While enzymatically resistant nucleotide analogs might appear to be particularly useful as potential antivirals, their polar character prevents effective entry of these analogs into the cells, as does lack of appropriate nucleotide receptors at the cellular membrane.

This difficulty appears to be overcome in the series of acyclic nucleotide analogs which contain an aliphatic chain, bearing hydroxyl groups, replacing the sugar moiety. For example, the phosphates or phosphonic acid derivatives derived from the antiviral nucleoside analog ganciclovir (Cytovene) are reported to possess an anti-herpes virus activity (Reist at al., in "Nucleotide Analogs as Antiviral Agents", ACS Symposium Series, No. 401, pp. 17–34 (1989); Tolman, ibid, pp. 35–50; Prisbe et al., *J Med Chem* (1986), 29:671).

The following formulas describe several classes of prior art compounds:

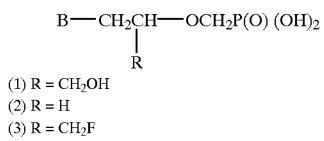

(1) R = CH₂OH
(2) R = H
(3) R = CH₂F

Another group of antiviral compounds where the antiviral action is less strictly limited by the nature of the heterocyclic base includes phosphonic acid analogs in which a phosphonic acid moiety is linked to the hydroxyl group of an aliphatic chain sugar substitute via a methylene unit. Examples of such compounds are HPMP-derivatives (1) which were disclosed by the UK Patent Application No. 2 134 907 and PV-3017, now published on Dec. 30, 1986 as EP 206,459 of Holý et al. Such compounds act exclusively against DNA viruses as reported by De Clercq et al. in *Nature* (1986) 3:464–467, and reviewed by Holý et al. in *Antiviral Res* (1990) 13:295.

A similar type of antivirals is represented by PME-derivatives (2) disclosed by European Patent Application 0 206 459 by Holý et al. and described in detail by De Clercq at al. in *Antiviral Res* (1987) 8:261, and by Holý et al. in *Collection Czech Chem Commun* (1987) 52:2801; ibid. (1989), 54:2190). These compounds act against both DNA viruses and retroviruses, including HIV-1 and HIV-2. The adenine derivative, PMEA, was demonstrated to exhibit an outstanding activity against Moloney sarcoma virus in mice, simian immunodeficiency virus in Rhesus monkeys as well as feline immunodeficiency virus in cats (Balzarini et al., *AIDS* (1991) 5:21; Egberink et al., *Proc Natl Acad Sci U.S.A.* (1990) 87:3087).

The extensive structure-activity investigation which concentrated on the modification of the side-chain (described by Holý et al. in "Nucleotide Analogs as Antiviral Agents", ACS Symposium Series No.401 (1989), p. 51) did not reveal any additional substantially active antivirals. Replacement of this hydroxyl by fluorine atom resulted in the FPMP-compounds (3) which, in addition to having some anti-DNA-virus activity display a substantial effect on both HIV-1, HIV-2 and murine sarcoma virus (as taught by Holý et al., Czechoslovak Patent Application PV 2047-90 now published on Oct. 30, 1991 as EP 454,127, and by Balzarini et al., *Proc Natl Acad Sci U.S.A.* (1991) 88:4961).

The racemic mixtures of 9-(2-phosphonomethoxypropyl)adenine and guanine (PMPA and PMPG) were also described by Holý et al., European Patent Appl. 0206459 (PMPA) and Holý et al., *Collection Czech Chem Commun* (1988) 53:2753 (PMPA), and by U.S. patent application Ser. No. 932,112 (PMPG). PMPA was devoid of any appreciable antiherpetic effect while any antiherpetic activity of PMPG appeared due to its substantial cytotoxicity. The clinical forms of PMPG, and of the related compound, 9-(3-hydroxy-2-(phosphonomethoxy)propyl)guanine (HPMPG) are disclosed in EP application 452935. For these guanine forms, the R-enantiomers consistently gave greater antiviral activity, especially in regard to the retrovirus HIV. There was little difference between R&S enantiomers in antiviral activity with regarding to some DNA viruses. It cannot be predicted whether this pattern of activity would extend to PMP compounds of other than guanine.

Nothing in the above-cited references or their combination permits any prediction that the resolved enantiomers of the present invention would exhibit antiretroviral activity, or what the enantiomers preference would be.

SUMMARY OF THE INVENTION

Resolved enantiomeric forms of N-(2-phosphonomethoxypropyl) derivatives of purine and pyrimidine bases have been synthesized and found to possess useful and unexpected antiviral activity which is directed specifically against retroviruses. These compounds are of the formulas IA and IB, wherein IA represents the R enantiomer and IB represents the S enantiomer.

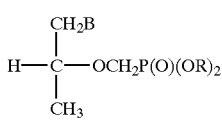
(IA)

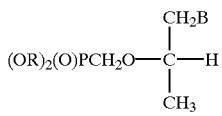
(IB)

In the formulas IA and IB, B is a purine or pyrimidine base or aza and/or deaza analog thereof except for guanine and R is independently H, alkyl(1–6C), aryl or aralkyl.

Thus, in one aspect, the invention is directed to compositions comprising Formula IA unaccompanied by any substantial amount of the corresponding compound of Formula IB and to compositions comprising a compound of the Formula IB unaccompanied by any substantial amount of the corresponding compound of the formula IA.

By "any substantial amount" is meant less than about 5 mole %, preferably less than about 2 mole %, more preferably less than about 1 mole % and most preferably in undetectable amounts. By "corresponding compound" is meant the enantiomer of the compound shown.

Other aspects of the invention include the preparation of these compositions, their formulation into antiviral pharmaceutical compositions and the use of these formulations to treat retroviral infections.

DETAILED DESCRIPTION OF THE INVENTION

The compounds of the invention are the resolved (R) and (S)-enantiomers of N-(2-phosphonomethoxypropyl) derivatives of purine and pyrimidine bases which have structural formula I.

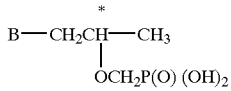
(I)

B is a purine or pyrimidine base or an aza and/or deaza analog thereof other than guanine. Renantiames are preferred. As used herein, "purine" refers to substituted or unsubstituted moieties of the formula (in the following, free valences and hydrogen are not shown):

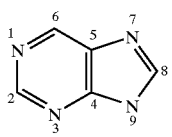

and "pyrimidines" to substituted or unsubstituted moieties of the formula

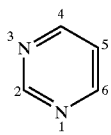

In aza analogs, at least one C shown in the above formulas is replaced by N; in deaza analogs, at least one N is replaced by C. Combinations of such replacements are also included within the scope of the invention.

Thus, 1-deaza purine analogs are of the formula

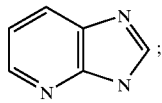;

3-deaza purine analogues are of the formula

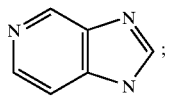;

8-aza purine analogs are of the formula

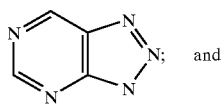; and 1-deaza-8-aza purine analogs are of the formula

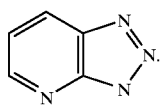.

Preferred embodiments of B are those wherein B is a purine base selected from the group consisting of adenine, 2,6-diaminopurine, 2-aminopurine, hypoxanthine, xanthine; and their 1-deaza, 3-deaza or 8-aza analogs; and derivatives of purine or said analogs, which derivatives are other than guanine, substituted at position 2 and/or 6 and/or 8 by amino, halogen, hydroxy, alkoxy, alkylamino, dialkylamino, aralkylamino, heteroaralkylamino, hydroxyamino, alkoxyamino, hydrazino, heterocyclic amino, azido, mercapto or alkylthio.

For the purposes herein it is understood that tautomeric forms are included in the recitation of a given group, e.g., thio/mercapto or oxo/hydroxyl.

Included in this invention are those embodiments wherein B is a pyrimidine base selected from the group consisting of cytosine, uracil, thymine, 5-methylcytosine, and their 6-aza analogs; and derivatives of pyrimidine substituted at the exocyclic amino group in position 4 by alkyl, aralkyl, hydroxy or amino.

As used herein, halogen refers to F, Cl, Br or I; alkyl refers to a straight- or branched-chain saturated hydrocarbyl group containing 1–6C, such as methyl, ethyl, 2-propyl, n-pentyl, neopentyl and the like; alkoxy is a group of the formula $-OR_1$ wherein $R_1$ is alkyl as above defined; alkylthio is a group of the formula —SR$_1$ wherein R$_1$ is alkyl as above defined; aralkyl or heteroaralkyl is a group of the formula —R$_1$—Ar wherein —R$_1$— is the alkylene counterpart of alkyl(—R$_1$) as above defined, Ar is a substituted (with hydroxyl, halo, amino, sulfonyl, carbonyl or C1–C3 alkyl substituted with hydroxyl, halo, amino, sulfonyl or carbonyl) or unsubstituted aromatic group having 6–10C and optionally a heteroatom selected from oxygen or nitrogen, e.g., phenyl, napthyl, quinolyl and benzyl; aralkyl amino or heteroaralkyl amino means groups of the formula —N(Z)$_2$ wherein Z independently is H or —R$_1$—Ar (but at least 1 Z is —R$_1$—Ar); heterocyclic amino is a saturated or unsaturated heterocyclic ring containing at least 1 N atom (ordinarily 1) and optionally in addition at least 1 other heteroatom (examples being pyrrolidine, morpholino, piperidine and the like radicals). Typically, cyclic structures contain from 3 to 6 ring atoms and are monocyclic. In some embodiments, the substituents of purine 6-amino groups are taken together with purine N$_1$ to form an N-heterocycle fused to the purinyl moiety, for example as in N1, N6-etheno-adenine.

The compounds of the invention can be isolated in the form of free acids, salts or, in the case of compounds with heterocyclic bases bearing at least one amino function, in the form of zwitterions. The acid or zwitterionic forms can be obtained on purification of the deionized crude material by anion exchange chromatography, using volatile organic acids (acetic or formic acid) as eluents. The free acid forms can be easily transformed into physiologically acceptable salts by methods known in the art. Such salts include those of ammonium ion, Li$^+$, Na$^+$, K$^+$, Mg$^{++}$ and Ca$^{++}$ or pharmaceutically acceptable organic cations; the salts may be monobasic or dibasic. Compounds with at least one amino function contained in B can also be prepared as the acid addition salts inorganic or organic acids, such as HBr, HCl, H$_2$SO$_4$ or HOAc.

In certain cases, the acid or zwitterionic forms of compounds of the Formula IA and IB are extremely water-insoluble. Under such circumstances, purification is performed on a medium basic anion exchanger (e.g., DEAE-cellulose, DEAE-Sephadex) in a weakly alkaline volatile buffer, such as triethylammonium hydrogen carbonate. The resulting water-soluble triethylammonium salts can be transformed to salts of other cations by, e.g., cation exchange, using cation exchanger in the corresponding form.

The free acids, zwitterions or salts of compounds of Formula IA or IB are stable in the solid state or in sterile aqueous or aqueous-alcoholic solutions.

Methods of Preparation

The compounds of this invention can be prepared from an easily prepared chiral intermediate X derived from resolved lactic acid ester enantiomers using reaction scheme 1 or 2.

Reaction scheme 1 is as follows:

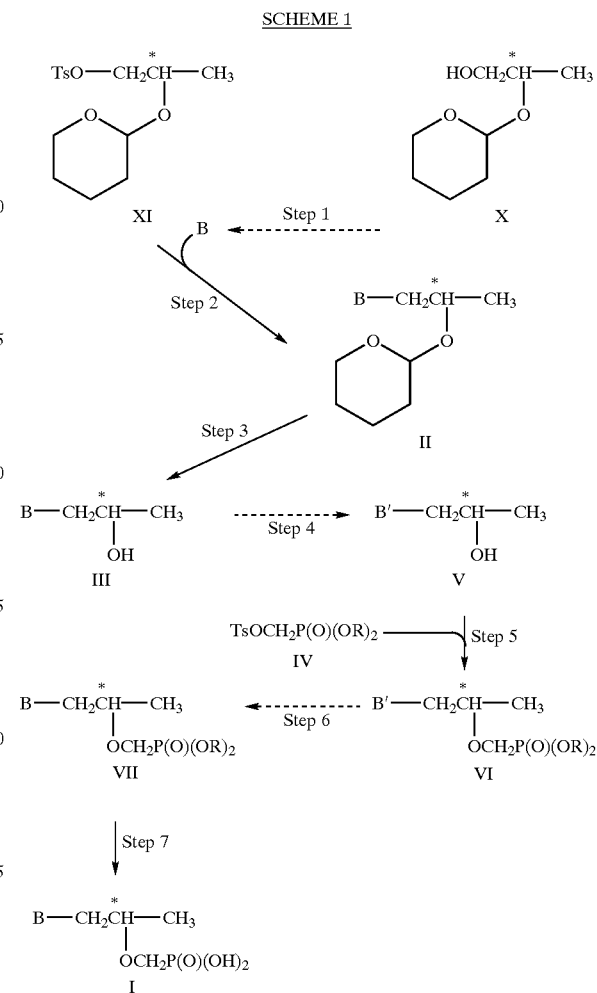

wherein B is as defined above and B' is its suitably protected form; the * above the chiral center indicates that the resolved enantiomer is used.

Protection of B comprises blocking of active hydrogen atoms contained in B, such as any hydroxy, amino or carbamido group. Protection can be achieved by introduction of alkali-labile groups, such as acetyl, benzoyl, pivaloyl or amidine, such as a dimethylaminomethylene group, or, by acid-labile groups such as trityl, substituted trityl, tetrahydropyranyl groups and the like.

The desired enantiomer of 2-O-tetrahydropyranylpropane-1,2-diol of the Formula X is transformed to the corresponding 1-O-p-toluenesulfonyl esters in Step 1 under usual conditions, i.e. reaction with p-toluenesulfonyl chloride in pyridine. The tosyl group shown is preferred, however standard organic leaving groups such as mesylate, triflate or halide can also be used.

The protected intermediate of the Formula XI, isolated either by direct crystallization or by silica gel chromatography, occurs as a mixture of diastereomers which gives complex NMR spectra.

The alkylation of a heterocyclic base with the synthon of the Formula XI in Step 2 is mediated by the formation of an anion which can be generated either by pretreatment of the base with alkali hydride in an inert solvent, such as dimethylformamide, or, by the anion formation generated in situ by alkali carbonate. In the latter case, an importance of cesium carbonate as a catalyst must be recognized. This catalyst not only substantially accelerates the alkylation of the base, it also favorably influences the regiospecificity of alkylation by the synthon XI in purine ring systems, giving alkylation at the preferred N9 position of purines or the corresponding position in the aza or deaza bases.

The tetrahydropyran-2-yl group is cleaved in acidic media to afford the intermediate III in Step 3. This cleavage can be achieved by the action of mineral acid (e.g. sulfuric acid) anion exchange resins or organic acids (e.g. acetic acid, formic acid) followed by deionization.

The N-(2-hydroxypropyl) derivatives of Formula III are transformed in Step 4 to base-protected derivatives of Formula V using any of a variety of methods generally available for the purpose, such as selective N-acetylation, N-benzoylation, reaction with dimethyformamide dialkyl acetals, N-tritylation, reaction with 3,4-dihydro-2H-pyrane and the like.

In Step 5 of Scheme 1 the protected intermediate of Formula V is converted to the alkoxide anion by treatment with a suitable base, such as alkali metal hydride, in a non-reactive solvent, such as dimethylformamide, and the alkoxide is treated with dialkyl p-toluenesulfonyloxymethylphosphonate (Formula IV). Preferably the phosphonate esters are of 2-propyl alcohol. The reaction is performed by stirring a mixture of the Formula V intermediate with the tosyl derivative of Formula IV in the presence of three, equivalents (relative to intermediate V) of alkali hydride, e.g., NaH or KH or other suitable reagents at temperatures ranging from −10° to 80° C., mostly from 0° C. to 20° C. The reaction lasts from several hours up to several days, depending on the nature and concentration of the reaction components. Since gaseous hydrogen is evolved during the reaction, it is essential to work in an open system with suitable protection against moisture.

Protecting groups are then removed from B' and the phosphonate ester linkages are hydrolyzed. Removal of the protecting groups from B' in Step 6 can be achieved by generally acceptable methods such as methanolysis, acid hydrolysis, etc. Alkali labile groups can be removed simply by dilution of the mixture with methanol. The resulting diester of Formula VII is isolated by silica gel chromatography, or using other suitable supports, or contaminating non-nucleotide materials may be removed by deionization on cation exchangers, such as Dowex 50, or, by hydrophobic silica chromatography. The purified intermediate of Formula VII is then hydrolyzed, in Step 7 for example, by treating with a halotrialkylsilane, such as bromotrimethylsilane or iodotrimethylsilane in a polar aprotic solvent such as acetonitrile or DMF for 4–20 hours at room temperature. Volatiles are then evaporated in vacuo and the final product may then be obtained by further purification and isolation techniques depending upon its character. Ion exchange chromatography making use of the presence of negatively charged phosphonate group is preferred.

Alternatively, compounds of Formula I can be prepared by Reaction Scheme 2.

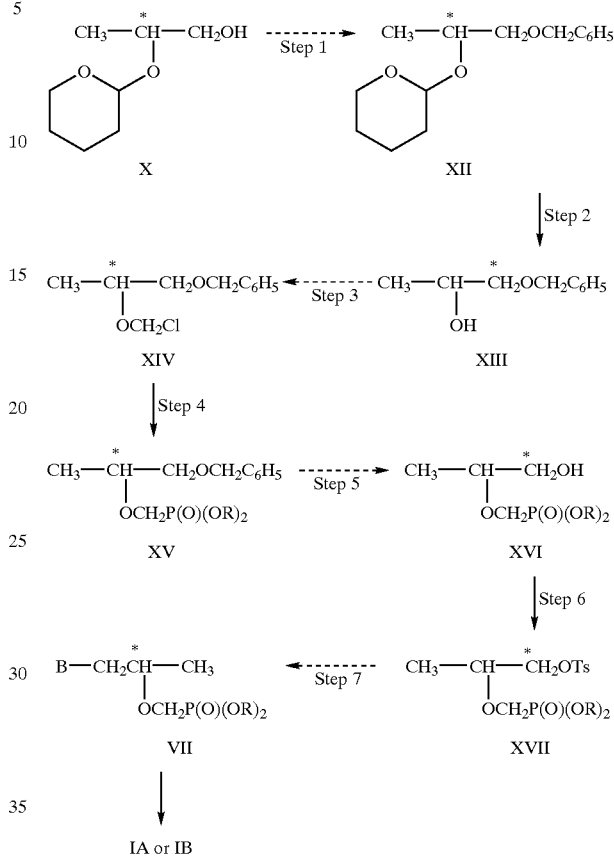

In Scheme 2, the synthon of Formula XVII is ultimately used to provide the chiral PMP precursor. It bears a leaving tosyl group and can be used for alkylation of the heterocyclic base or its protected derivative to afford Formula VII, the protected diester form of the compounds of the invention.

In Reaction Scheme 2, as in Reaction Scheme 1, a resolved form of 2-O-(tetrahydropyranyl)-propane-1,2-diol of the Formula X provides the required resolved enantiomer. The resolved compound of Formula X affords, in Step 1, on benzylation under standard conditions, e.g. with benzyl bromide in the presence of sodium hydride in DMF, the benzyl ether XII which is then transformed by acid hydrolysis in Step 2 to the resolved enantiomeric 2-O-benzylpropane-1,2-diol of the Formula XIII. Either enantiomer (a distillable oil) affords, in Step 3, on chloromethylation with 1,3,5-trioxane or paraformaldehyde in the presence of hydrogen chloride an intermediary chloromethyl ether of the Formula XIV which is, without purification, transformed in Step 4 into the phosphonate diester XV by heating with tri(2-propyl)phosphite with simultaneous removal of 2-propyl chloride. Though the intermediate of the Formula XV is distillable in a high vacuum, this procedure may result in racemization. Partially purified products of this reaction are then hydrogenolysed under standard conditions such as hydrogenation in the presence of palladium-on-charcoal catalyst in methanol and the intermediary diester of the Formula XVI resulting from Step 5 is, without isolation, transformed in Step 6 into the tosyl derivative XVII by the action of tosyl chloride in pyridine.

The sequence X→XVII involves six steps, but does not require purification of the intermediates. All reactions proceed with high conversion so that the over-all yield of the sequence exceeds 40%. 2-propyl esters of the phosphonate are preferred, but other phosphonate protecting ester groups such as methyl, ethyl, benzyl and cyclic diesters can be used to the same effect. Also the tosyl group in the synthon of the Formula XVII could be replaced by other leaving groups, as for example mesyl, triflyl, p-nitrophenylsulfonyl, etc.

Step 7 of this synthetic sequence consists in the alkylation of the heterocyclic base by the synthon of the Formula XVII. It requires an equimolar amount of the base relative to the heterocycle. The alkylation is best performed in DMF at increased temperature with either a sodium salt generated from the heterocyclic base by sodium hydride reaction or, alternatively, with a mixture of the heterocyclic base and a slight excess of potassium carbonate or, to an advantage, cesium carbonate. The reaction can be made either with unprotected or protected (e.g. N-benzoylated) bases or their precursors as mentioned in the description of the reaction according to the Scheme 1.

The protected intermediates of the Formula VI can be applied to advantage for transformations at the heterocyclic base to afford a wide variety of additional compounds of the Formula I. The reactivity of the halogen (e.g. chlorine) atom at position 6 of the 2-amino-6-chloropurine, derivative'of the Formula VII is applicable for the preparation of a wide variety of 6-substituted 2-aminopurine compounds; thus, by heating with sodium or lithium azide it is possible to prepare the 2-amino-6-azidopurine derivative which can be further reduced to the 2,6-diaminopurine compound. Alternatively, treatment of the chloro derivative with thiourea affords the 6-thioguanine compound, whereas its reaction with primary or secondary amines provides N6-substituted or disubstituted 2,6-diaminopurine derivatives.

An analogous transformation is applicable also to the diester of the Formula VI derived from 6-chloropurine where it leads ultimately to the compounds of the Formula I containing 6-mercaptopurine or N6-mono- or disubstituted adenine.

The alkylation proceeds rapidly and the required intermediate of the Formula VII can be easily isolated from the reaction mixture and purified by chromatography. Further processing of these intermediates leading to the compounds of the Formula IA and IB is identical with the procedure described in the Scheme 1.

An advantage of this method of preparation of the Formula I compounds over the method described by the Scheme 1 consists, in addition to the possible avoidance of base protection, in the elimination of acidic conditions which are essential for the preparation of the intermediary N-(2-hydroxypropyl) derivatives of the Formula II, as well as of any other deprotection except for ultimate halotrimethylsilane treatment. The alternative procedure can thus be applied for the syntheses of compounds of the Formula I bearing sensitive heterocyclic bases.

In respect to both reaction Schemes 1 and 2, the compounds of the invention may be prepared by alkylation of the desired heterocyclic base B as shown, or, in certain cases, by alkylation of a precursor of B. Thus, guanine derivatives can be best synthesized via alkylation of 2-amino-6-chloropurine followed by acid hydrolysis of the C—Cl linkage. Cytosine derivatives can be synthesized by direct alkylation of cytosine in the presence of cesium carbonate in a modest yield; better yields are obtained by the ammonclysis of an intermediate formed by alkylation of 4-methoxy-2-pyrimidone with synthon XI.

Similar subsequent changes at the heterocyclic base can be performed with the final products of the Scheme, i.e. the compounds of Formula I which are the subjects of the invention: adenine, 2,6-diaminopurine or guanine derivatives can be transformed by deamination with nitrous acid or its esters to the corresponding hypoxanthine, 2-hydroxyadenine or xanthine derivatives; similarly, uracil derivatives can similarly be converted to cytosine derivatives. Further transformations of the compounds of the Formula I can be realized with routine methods of nucleic acid chemistry: e.g., reaction of the adenine moiety with chloroacetaldehyde will afford the N1,6-etheno derivatives; bromination of purine base to obtain the 8-bromo derivatives; N-alkylation of the NH— functions in both the purine and pyrimidine compounds, etc. None of these subsequent transformations concerns any changes at the side chain or the phosphonate group of the compounds of Formula I.

It will be recognized that the intermediate compounds that are parts of the pathways of Schemes 1 and 2 are themselves novel compounds and therefore are part of the invention.

An advantage of using the processes of Schemes 1 and 2 consists in the utilization of starting materials of the Formula X, which are easily available in optically pure forms. The reaction sequence to prepare the chiral synthon X used both in Scheme 1 and Scheme 2 is described in Scheme 3.

SCHEME 3

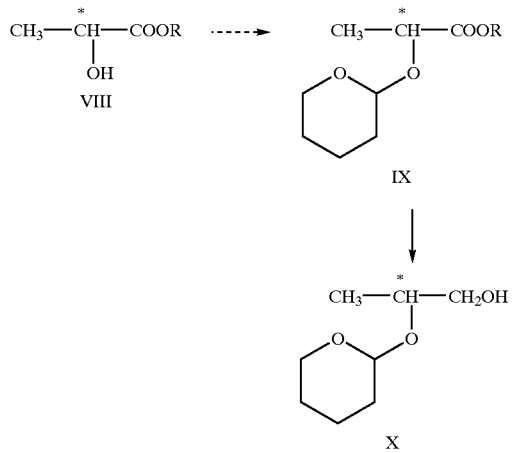

The crucial step of every asymmetric synthesis depends on the availability of optically pure chiral starting materials. The method used in the present invention makes use of commercially available (Merck) enantiomers of lactic acid alkyl esters of Formula VIII. These esters are first protected at the hydroxyl function by tetrahydropyranyl group; this reaction is performed without solvent by direct addition in the presence of an acid catalyst. The esters of the Formula IX are obtained by fractionation in vacuo. These intermediates are reduced by lithium aluminum hydride in ether or by bis(2-methoxyethoxy)aluminum hydride in ether or other inert solvents to the compounds of Formula X.

Biological Activity and Uses

The enantiomerically resolved compounds of the invention display significant antiretroviral activity both in vitro and in vivo. Their in vitro efficacy was demonstrated on human immunodeficiency virus type 1 (HIV-1) and type 2 (HIV-2) in MT4 and CEM cells, as well as on Moloney murine sarcoma virus (MSV) in C3H/3T3 cells. Their in vivo efficacy was proven in MSV infected NMRI mice, where the compounds markedly postponed the mean day of tumor initiation and substantially prolonged the mean survival day, both upon parenteral and oral administration.

The compounds of the invention have several advantages over the prototype compounds (PMEA, PMEADAP, PMEG) and/or FPMP derivatives, e.g., FPMPA, FPMP-DAP), and most relevant, unresolved PMPG+PMPA: (a) their antiretroviral activity is clearly separated from other antiviral activities (e.g. against herpes viruses); (b) their antiretroviral activity is not due to cellular toxicity. Consequently, the in vitro therapeutic index of these compounds is much higher than those of the prototype compounds and reaches a value of >2000 in some of the cases. Such compounds can be ideally suited to a long-term treatment of chronic diseases, e. g. AIDS.

The structures of the test compounds presenting the subject of this invention are completely unrelated to any of the compounds currently used in clinical trials of AIDS patients. This will avoid cross-resistance of these compounds against those virus strains that became resistant to such treatment, e.g., AZT, DDI, DDC, TIBO, nevirapine, pyridinohe, etc.

The biological activity of these compounds is highly enantiospecific. Generally, the (R)-enantiomers are responsible for the antiretroviral activity. The activity of (S)-enantiomers in the guanine series is accompanied by a substantially increased toxicity.

The compounds of the invention can be applied for the treatment of diseases caused by retroviruses, e.g. human immunodeficiency viruses (AIDS), human T-cell leukemia virus (hairy cell leukemia, acute T-cell leukemia (HTL)). Since the molecular target of antiviral action of these compounds is the virus-encoded reverse transcriptase, they should also have anti-hepadna virus activity (e.g. hepatitis B virus).

The compounds of this invention also are useful as intermediates in the preparation of other compounds useful in in vitro methods. For example, the compounds containing bases capable of Watson-Crick base pairing are diphosphorylated by known methods and employed as analogues to dideoxy NTP's heretofore conventionally used in nucleic acid sequencing. The compounds of this invention function as nucleic acid chain terminators, as do dideoxy NTPS. Other uses based on this property will be apparent to the ordinary artisan.

The compounds of this invention also are useful in preparative or diagnostic methods based on oligonucleotide or nucleic acid hybridization. For example, the compounds are converted to monomers suitable for incorporation into oligonucleotides using non-enzymatic synthetic methods, e.g. H-phosphonate or phosphoramidite chemistries. The monomers then are used as the 3' terminal base in oligonucleotide synthesis using such methods. The PMP portion of the monomer, any modified base present in the monomer, or both are readily available for recognition and binding by an antibody. The antibody in turn is labelled (for detecting hybridization of monomer-labelled probe to a target analyte sequence or the antibody is immobilized (for preparative separation of probe-bound nucleic acid). Exemplary methods of this sort are further described in EP 144,913,; EP 146,039; WO 85/02415,; UK 2,125,964A; they do not require that the monomers of this invention be capable of Watson-Crick base-pairing or that they be recognized by any polymerase.

The compounds may be administered topically or systemically i.e. orally, rectally, intravaginally and parenterally (by intermuscular, intravenous, subcutaneous and nasal routes). Generally, the oral application will require a larger quantity of the active ingredient to produce a therapeutic effect comparable with quantity given parenterally.

Pharmaceutical compositions for the treatment of human retroviral diseases will comprise at least one compound of the Formula IA or IB or a pharmaceutically acceptable salt thereof, generally comprising 95 to 0.5% wt/wt of the composition in combination with a pharmaceutically acceptable carrier and non-toxic inert adjuvant. Other therapeutic agents can also be present. Additionally, mixtures of compounds of formulas IA and/or IB can be employed, provided that each member of such mixture is substantially free of its enantiomer.

Pharmaceutical compositions containing compounds of the Formula I are conventionally prepared as tablets, lozenges, capsules, powders, aqueous or oil suspensions, syrups and aqueous solutions. The compounds can be formulated for a variety of modes of administration including systematic, topical or localized administration. Techniques and formulations generally may be found in *Remington's Pharmaceutical Sciences*, Mack Publishing Co., Easton, Pa., latest edition. The active ingredient is generally combined with a carrier such as a diluent orexcipient which may include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including transmuscular, intravenous, intraperitoneal, and subcutaneous. For injection, the compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

For topical administration, the compounds of the invention are formulated into ointments, salves, gels, or creams, as is generally known in the art. The compounds may also be administered for ophthalmic or ocular indications when appropriately formulated.

The effective dose of active compound of the present invention is expected to be about 0.01–50 mg/kg body weight with preferred range of 1 to 20 mg/kg. The dosage in clinical applications must be professionally adjusted considering age, weight and condition of the patient, the route of administration, the nature and gravity of the illness. Generally, the preparations are expected to be administered by oral route from about 100 mg to about 1000 mg per day, one to three times a day.

The compounds of the invention, their methods of preparation and their biological activity will appear more clearly from the examination of the following examples which are presented as an illustration only and are not to be considered as limiting the invention in its scope. All melting points have been estimated with the use of Kofler's block and are uncorrected. Solutions were evaporated at 40° C./2 kPa when not specified. Thin-layer chromatography was made with the use of silica plates containing fluorescent indicator; detection by UV-light. The nuclear magnetic resonance (NMR) spectral characteristics refer to chemical shifts (δ) expressed in parts per million (ppm) vs. tetramethylsilane (TMS) as reference compound. The multiplicity of signals is reported as singlet (s), doublet (d), doublet of doublets (dd), multiplet (m), triplet (t) or quartet (q); other abbreviations include broad (br) signal, aromatic protons (arom.), $d_6$-DMSO for hexadeuteriodimethylsulfoxide, $D_2O$ for deuterium oxide, NaOD for sodium deuteride and $CDCl_3$ for deuteriochloroform. Other abbreviations are conventional.

The following examples are intended to illustrate but not to limit the invention.

I. Synthesis of Intermediates of Formula II
A. Resolved Formula XI Precursors

EXAMPLE 1

(R)-2-O-Tetrahydropyranyl-1-O-p-toluenesulfonylpropane-1,2-diol

A mixture of isobutyl (R)-lactate (73 g, 0.5 mol, Merck) and 3,4-dihydro-2H-pyran (70 g, 0.83 mol, Merck) was treated with 5M hydrogen chloride in dimethylformamide (4 ml) and set aside at ambient temperature overnight in calcium chloride protected 250 ml round-bottom flask. Silver oxide (15 g) was added, the mixture stirred magnetically for 2 hours and then filtered. The product was isolated by distillation (13 Pa, b.p. 94∝96° C.) to provide isobutyl 2-O-tetrahydropyranyl-(R)-lactate (102.5 g, 89%) as a colorless oil.

A 1 l 3-necked round-bottomed flask was oven dried and equipped with reflux condenser with calcium chloride protection tube, 250 ml dropping funnel and magnetic stirring rod. It was then charged with a suspension of lithium aluminum hydride (15.8 g, 0.415 mol) and ether (500 ml, distilled from phosphorus pentoxide) and placed in ice-water bath.

A solution of isobutyl 2-O-tetrahydropyrany-(R)-lactate was added dropwise under stirring at such a speed that the mixture was continuously in mild reflux (approx.30 min.). The cooling bath was removed and the mixture stirred in reflux for additional 3 hours by applying an external heating. It was then cooled again by ice-water bath and ethyl acetate (75 ml) was added during 20 minutes followed by water (15 ml) and 4M NaOH (15 ml). The resulting mixture was then filtered by suction over a layer of Celite 521 (Janssen) and washed with chloroform (500 ml). The combined filtrate was taken down in vacuo, the residue redissolved in ether (300 ml) and anhydrous magnesium sulfate (50 g) added. After standing overnight at ambient temperature, the mixture was filtered by suction, washed with ether (200 ml) and the filtrate stripped of the solvent in vacuo. The remaining oil afforded by distillation (13 Pa, 75–76° C.) 2-O-tetrahydropyranyl-(R)-propane-1,2-diol (67.5 g, 0.422 mol, 95%) as a colorless oil.

A solution of 2-O-tetrahydropyrany-(R)-propane-1,2-diol (67.2 g, 0.42 mol) in pyridine (600 ml) was placed in a 2 l round-bottom flask with magnetic stirring rod and 500 ml dropping funnel with a side-tubing, protected by calcium chloride tube. 4-Dimethylaminopyridine (2 g) was added, the flask was placed in an ice-water cooling bath and a solution of p-toluenesulfonyl chloride (91 g, 0.477 mol) in pyridine (300 ml) was added over 1 hour under stirring. The mixture was stirred under ice-cooling for additional 3 hours and left to stand overnight in a refrigerator at 4° C. Water (20 ml) was then added to the mixture and, after standing for 1 hour, pyridine (approx. 300 ml) was distilled off in vacuo. The residue was diluted by ethyl acetate (2.5 l) and shaken with water (300 ml). After separation of the lower aqueous layer, the organic phase was washed with water (two 300 ml portions), evaporated in vacuo and the residue co-evaporated with toluene (four 250-ml-portions) in vacuo. The remaining amber oil was purified by chromatography over silica gel (eluting with chloroform) to afford 122 g (0.39 mol, 93%) of (R)-2-O-tetrahydropyrany-1-O-p-toluenesulfonylpropane-1,2 diol as a thick colorless oil, $R_F$ 0.60 (TLC, chloroform). This product was stored at +4° C. for several months without obvious decomposition. For $C_{15}H_{22}OS$ (MW 314,4) calculated: C,57.30; H,7.05; S,10.20. Found: C,57.15; H,7.22; S,10.52.

EXAMPLE 2

(S)-2-O-Tetrahydropyranyl-1-O-p-toluenesulfonylproyane-1,2-diol

A mixture of ethyl L-(−)lactate (59 g, 0.5 mol, Merck) and 3,4-dihydro-2H-pyran (70 g, 0.83 mol) was treated and worked up exactly as described in Example 1 to afford, after distillation (2 kPa, 102–104° C.) ethyl 2-O-tetrahydropyrany-(S)-lactate (98 g, 0.485 mol, 97%) as a colorless oil.

This material (91 g, 0.45 mol) was treated with lithium aluminum hydride as described in Example 2 to afford after distillation (13 Pa, 72–75° C.) 2-O-tetrahydropyrany-(S)-propane-1,2-diol (67.7 g, 0.423 mol, 94%) as a colorless oil.

Following the conditions described in Example 1,2-O-tetrahydropyrany-(S)-propane-1,2-diol (67.2 g, 0.42 mol) was transformed in (S)-2-O-tetrahydropyrany-1-O-p-toluenesulfonylpropane-1,2-diol. The purification by chromatography on silica gel (elution by chloroform) gave the product (121 g, 0.386 mol, 92%) as a thick colorless oil, chromatographically (TLC, $R_F$ 0.60 in chloroform) homogeneous. For $C_{15}H_{22}O_5S$ (MW 314,4) calculated: C,57.30; H,7.05; S,10.20. Found: C,57.50; H,7.33; S,9.95.

B. Formula II Compounds

EXAMPLE 3

9-(S)-(2-Hydroxypropyl)adenine

A suspension of finely ground adenine (13.6 g; 0.1 mol) and cesium carbonate (16.4 g; 0.05 mol) in dimethylformamide (400 ml, distilled from phosphorus pentoxide) was placed in 1 l round-bottom flask equipped with 250 ml dropping funnel and calcium chloride protecting tube. The mixture was preheated at 100° C. and a solution of (S)-(2-O-tetrahydropyrany-1-O-p-toluenesulfonyl)propane-1,2-diol (31.4 g, 0.1 mol) in dimethylformamide (200 ml) was added dropwise under magnetic stirring over 30 minute period. The resulting clear solution was heated at 100° C. for additional 6 hours, cooled down and the solvent distilled off at 50° C./13 Pa. The residue was extracted with boiling chloroform (three 300-ml-portions), filtered and the filtrate taken down in vacuo. The residue afforded by crystallization from boiling ethanol 9-(S)-(2-O-tetrahydropyranyloxypropyl)adenine (13.2 g, 0.048 mol, 48%) m.p. 172° C. $R_F$ 0.40 (TLC, chloroform-methanol, 4:1). For $C_{13}H_{19}N_5O_2$ (277.3) calc. C, 56.30; H, 6.91; N, 25.26. found C, 56.46; H, 6.82; N, 25.57. $^1$H-NMR (200 MHz, d6-DMSO): H2,H8 : 2×s, 8.14 and 8.04; NH2: br s, 7.20; 1'-CH$_2$: dd, 1H, 4.23 (J1,2=3.2, Jgem=13.7) and dd, 1H, 4.11 (J1,2=7.1): 2'-CH: m, 1H, 4.06; 3'-CH$_3$: d, 3H, 1.12 (J3,2=6.1); tetrahydropyranyl 1"-CH: dd, 1H, 4.28 (J=2.9, 4.4); 5-CH$_2$: ddd, 1H, 3.72 (J=3.9, 7.8, 11.5) and ddd, 1H, 3.34 (J=4.9, 5.1, 11.2); additional CH$_2$: m, 6H, 1.20–1.65.

A solution of 9-(S)-(2-O-tetrahydropyranyloxypropyl)adenine (13 g, 0.047 mol) in 0.25M sulfuric acid (300 ml) was left to stand overnight at ambient temperature and neutralized with saturated aqueous barium hydroxide solution to pH 7.0–7.1 (with the use of pH-meter). The resulting suspension was brought to 80° C. and after standing for 30 minutes filtered through a layer of Celite 521 (Janssen) and the precipitate washed with boiling water (500 ml). The combined filtrate and washings were evaporated to dryness in vacuo, the residue coevaporated with ethanol (two 200 ml portions and crystallized from boiling ethanol (ether added to turbidity). The product was collected by filtration to give 9-(S)-(2-hydroxypropyl)adenine (7.7 g, 0.04 mol, 85%), m.p.202° C. For C$_8$H$_{11}$N$_5$O (MW 193,2) calc.: C, 49.73; H, 5.74; N, 36.25. found C, 49.59; H, 5.54; N, 36.29. [α]$_D$=−41.0° (c=0.5, 0.1M HCl). $^1$H-NMR (200 MHz, d$_6$-DMSO): H2,H8:2×s, 2H, 8.14 and 8.05; NH$_2$: br s, 2H, 7.23; OH: br,1H, 5.05 (J$_{OH,CH}$=4.2); N—CH$_2$+O—CH: m, 3H, 3.97–4.13; CH$_3$: d, 3H, 1.06 (J$_{CH3,CH}$=5.6).

EXAMPLE 4

9-(R)-(2-Hydroxypropyl)adenine

The condensation of adenine (13.6 g, 0.1 mol) and (R)-(2-O-tetrahydropyrany-1-O-p-toluenesulfonylpropane-1,2-diol (31.4 g, 0.1 mol) was performed in the presence of cesium carbonate (16.4 g, 0.05 mol) as described in Example 3. After extraction by boiling chloroform, the crystallization of the residue from ethanol (ether added to turbidity) afforded 9-(R)-(2-O-tetrahydropyranyloxypropyl)adenine (14.6 g, 0.053 mol, 53%), m.p.171–172° C. For C$_{13}$H$_{19}$N$_5$O$_2$ (277.3) calc. C, 16.30; H, 6.91; N, 25.26. found C, 56.57; H, 6.71; N, 25.41. $^1$H-NMR spectrum (200 MHz, d$_6$-DMSO) closely resembles to that of 9-(S)-(2-tetrahydropyranyloxypropyl)adenine (Example 3).

A solution of 9-(R)-(2-tetrahydropyranyloxypropyl)adenine (14.0 g, 0.05 mol) in 0.25 M sulfuric acid was left to stand overnight at ambient temperature and worked-up as described in Example 3. The product was isolated to give 9-(R)-(2-hydroxypropyl)adenine (8.1 g, 0.042 mol, 84%), m.p. 202° C. For C$_8$H$_{11}$N$_5$O (MW 193,2) calc. C, 49.73; H, 5.74; N, 36.25. found C, 49.80; H, 5.64; N, 36.44. $^1$H-NMR spectrum (200 MHz, d$_6$-DMSO) is identical with that of the (S)-enantiomer (Example 9). [α]$_D$=+40.8° (c=0.5, 0.1M HCl).

EXAMPLE 5

9-(R)-(2-hydroxypropyl)-2,6-diaminopurine

A suspension od 2,6-diaminopurine (15 g, 0.1 mol) and cesium carbonate (16.4 g, 0.05 mol) in dimethylformamide (250 ml) was placed in 500 ml round-bottom flask with magnetic stirring rod and calcium chloride protecting tube and preheated to 100° C. (R)-(2-O-tetrahydropyrany-1-O-p-toluenesulfonylpropane-1,2-diol (32.8 g, 0.104 mol) was added in one portion and the mixture stirred at 100° C. for 20 hours. The solvent was evaporated at 50° C./13 Pa and the residue extracted with boiling chloroform (three 300-ml-portions). The filtrate was separated on silica gel column (500 ml), the product eluted by chloroform-methanol mixture (95:5), affording, after crystallization from ethyl acetate (ether added to turbidity), 9-(R)-(2-tetrahydropyranyloxypropyl)-2,6-diaminopurine (14.2 g, 0.0485 mol, 48.5%), m.p.150–152° C. For C$_{13}$H$_{20}$N$_6$O$_2$ (292.3) calc. C, 53.41; H, 6.90; N, 28.76. found C, 53.27; H, 7.02; N, 28.77.

A solution of 9-(R)-(2-tetrahydropyranyloxypropyl)-2,6-diaminopurine (11.7 g, 0.04 mol) in 0.25M sulfuric acid (400 ml) was left to stand overnight at ambient temperature, neutralized with aqueous ammonia and concentrated in vacuo. The solution was applied onto a column of Dowex 50x8 (250 ml, 100–200 mesh, acid form) and the column washed with water until the UV-absorption and conductivity of the eluate dropped to the original values. The product was eluted by diluted (1:10) aqueous ammonia, the UV-absorbing eluate was collected and taken down in vacuo. The residue gave on crystallization from ethanol 9-(R)-(2-hydroxypropyl)-2,6-diaminopurine (6.5 g, 0.031 mol, 77.5%), m.p. 192° C. For C$_8$H$_{12}$N$_6$O (208.2) calc. C, 46.15; H, 5.81; N, 40.37. found C, 45.97; H, 5.72; N, 40.56. $^1$H-NHR-spectrum (200 MHz, d$_6$-DMSO): H-8, 1H, 7.62; NH$_2$: 2×br s, 2×2H, 6.65 and 5.77; OH: br, 1H, 5.05; 1'-CH$_2$: dd, 1H, 3.90 (J$_{1,2}$=3.9, J$_{gem}$=13.7) and 3.80, dd 1H (J$_{1,2}$=7.6, J$_{gem}$=13.7); 2'-CH: m, 1H, 3.95; 3'-CH$_3$: d, 3H, 1.04 (J$_{3,2}$=6,19). [α]$_D$=−40.7° (c=0.5, 0.1M HCl).

EXAMPLE 6

9-(S)-(2-Hydroxypropyl)-2,6-diaminopurine

The synthesis was performed in analogy to Example 5, with (S)-2-O-tetrahydropyrany-1-O-p-toluenesulfonylpropane-1,2-diol (34.5 g, 0.11 mol). The crude reaction product was dissolved in 0.25 M sulfuric acid (300 ml) and left to stand overnight at ambient temperature. The mixture was alkalized by ammonia and evaporated in vacuo to a volume of approx. 150 ml which was then applied onto a column (300 ml, 100–200 mesh) of Dowex 50x8 (acid form). The column was washed thoroughly with water till the disappearance of UV-absorption of the eluate. Subsequent elution with dilute (1:10) ammonia afforded UV-absorbing fraction which was taken down in vacuo and crystallized from methanol to give crude 9-(S)-(2-hydroxypropyl)-2,6-diaminopurine (content, >95%; 9.2 g, 0.044 mol, 44%) which was used in the subsequent synthetic step. [α]$_D$=+41.2° (c=0.5, 0.1M HCl).

EXAMPLE 7

9-(R)-(2-Hydroxypropyl)quanine

A suspension of 2-amino-6-chloropurine (18.6 g, 0.11 mol, Mack) and cesium carbonate (17.9 g, 0.055 mol) in dimethylformamide (350 ml) was stirred at 100° C. under calcium chloride protection tube and a solution of (R)-(2-O-tetrahydropyranyl-1-O-p-toluenesulfonylpropane-1,2-diol (42 g, 0.134 mol) in dimethylformamide (100 ml) was added dropwise over 30 min. interval. The mixture was stirred at 100° C. for additional 6 hours, cooled and evaporated at 50° C./13 Pa. The residue was extracted with boiling chloroform (three 300-ml-portions) and the extract concentrated in vacuo. This material was applied onto a column of silica gel (500 ml) in chloroform and eluted by the same solvent. The relevant UV-absorbing fractions were pooled, evaporated and dried in vacuo. 9-(R)-(2-tetrahydropyranyloxypropyl)-2-amino-6-chloropurine was obtained as yellow amorphous foam, R$_F$ 0.64 (TLC in chloroform-methanol, 95:5) (10.7 g, 0.034 mol, 31%). For $C_{13}H_{18}ClN_5O_2$ (311.8) calc.: C, 50.08; H, 5.82; Cl, 11.37; N, 22.47. found C, 49.92; H, 6.08; Cl, 11.44; N, 22.54. $^1$H-NMR spectrum (200 MHz, d6-DMSO): H-8: S, 1H, 8.06; 1'-$CH_2$: dd, 1H, 4.01 ($J_{1',2'}$=7.3, $J_{gem}$=14.2) and dd, 1H, 3.94 ($J_{1'',2'}$=5.4, $J_{gem}$=14.2); 2'-CH: m, 1H, 3.42; 3'-$CH_3$: d, 3H, 1.06 ($J_{3',2'}$=5.4); tetrahydropyranyl: 1''-CH: dd, 1H, 5.07 (J=2.9, 8.3); 5''-$CH_2$: m, 4.02 and dt, 1H, 3.80 (J=2.0, 2.0, 11.7); other $CH_2$: m, 1.30–1.90.

A solution of 9-(R)-(2-tetrahydropyranyloxypropyl)-2-amino-6-chloropurine (10 g, 0.032 mol) in 1M hydrochloric acid (200 ml) was refluxed under stirring for 1 hour, cooled, alkalized with ammonia and evaporated in vacuo. The residue was crystallized from boiling water (decolorized with active charcoal) to afford 9-(R)-(2-hydroxypropyl) guanine (6.0 g, 0.029 mol, 91%), m.p.255° C. For $C_8H_{11}N_5O_2$ (209.2) calc. C, 45.92; H, 5.30; N, 33.48. found C, 46.02; H, 5.25; N, 33.41. $^1$H-MNR spectrum (200 MHz, d$_6$-DMSO): NH: br, 1H, 10.80; H-8: s, 1H, 7.61; $NH_2$: br s, 2H, 6.74; OH: br, 1H, 5.05; 1'-$CH_2$: dd, 1H, 3.89 ($J_{1',2'}$=3.7, $J_{gem}$=13.4) and dd, 1H, 3.78 ($J_{1'',2'}$=7.8, $J_{gem}$=13.4); 3'-$CH_3$: d, 3H, 1.03 ($J_{3',2'}$=6.1) $[\alpha]_D$=−35.7° (c=0.5, 0.1M HCl).

EXAMPLE 8

9-(s)-(2-Hydroxypropyl)quanine

To a slurry of 4 g (0.1 mol) of 60% NaH dispersion in mineral oil(Janssen) in distilled dimethylformamide (300 ml) in a 1 l-round-bottom flask equipped with calcium chloride protecting tube was added in one portion 2-amino-6-chloropurine (17.5 g, 0.1 mol,Mack) and the mixture was magnetically stirred for 1 hour at ambient temperature. (S)-(2-O-Tetrahydropyrany-1-O-p-toluenesulfonylpropane-1,2-diol (34.5 g, 0.11 mol) was then added in one portion and the mixture stirred at 60° C. for 3 hours and at 80° C. for 8 hours. The solvent was then removed at 50° C./13 Pa and the residue triturated with boiling chloroform (two 300 ml portions) and filtered. The filtrate was chromatographed on a silica gel column (300 ml) to give 9-(S)-(2-O-tetrahydropyranyloxypropyl)-2-amino-6-chloropurine (10.9 g, 0.035 mol, 35%) as an amorphous foam. This material was refluxed in a mixture of 2M hydrochloric acid (100 ml) and dioxane (100 ml) for 1 hour, cooled, neutralized with aqueous ammonia and evaporated in vacuo. The residue afforded by crystallization from water (decolorized with active charcoal) 9-(S)-(2-hydroxypropyl)guanine (5.7 g, 0.027 mol, 77%), m.p.256° C. For $C_8H_{11}$.$N_5O_2$ (209.2) calc. C, 45.92; H, 5.30; N, 33.48. found C, 45.88; H, 5.25; N, 33.41. $^1$H-NMR spectrum (200 MHz, d$_6$-DMSO) was identical with that of the (R)-isomer. $[\alpha]_D$=+36.2° (c=0.5, 0.1M HCl).

EXAMPLE 9

1-(R)-(2-Hydroxypropyl)cytosine

A mixture of cytosine (8.5 g, 76 mmol, Fluka), cesium carbonate (13 g, 40 mmol) and (R)-2-O-tetrahydropyrany-1-O-p-toluenesulfonylpropane-1,2-diol (24 g,76 mmol) in distilled dimethylformamide (300 ml) was stirred at 100° C. for 12 hours and filtered while hot. The filtrate was stripped off the solvent in high vacuum and the residue triturated with boiling chloroform (three 200-ml-portions) and filtered. The filtrate afforded by chromatography on a silica gel column to give 1-(R)-(2-tetrahydropyranyloxypropyl)cytosine (4.6 g, 18 mmol, 23.5%), m.p.259–260° C. (crystallized from ethyl acetate-petroleum ether mixture). For $C_{12}H_{19}N_3O_3$ (MW 253,3) calculated: C,56.89; H, 7.57; N, 16.59. found: C, 55.80; H, 7.72; N, 16.85. $^1$H-NMR (200 MHz, d$_6$-DMSO) (mixture of diastereomers, 3:1), major isomer: H-5: d, 1H, 5.73 ($J_{5,6}$=7.3), H-6: d, 1H, 7.52 ($J_{5,6}$=7.3); d, 3H, 1.13 (J=6.1), NH2: br s, 2H, 6.98; tetrahydropyranyl C-1'': br t, 1H, 4.36 (J=3.2); other $CH_2$ groups : m, total 10H, 1.20–1.70, 3.26–3.54, 3.72-4-01.

A solution of 1-(R)-(2-tetrahydropyranyloxypropyl) cytosine (4.0 g, 16 mmol) in 0.25 M sulfuric acid (50 ml) was left to stand at ambient temperature overnight and neutralized with saturated aqueous barium hydroxide solution to pH 7.0–7.1. The suspension was warmed to 80° C., filtered through a layer of Celite 521 (Janssen) and the filter washed with boiling water (500 ml). The filtrate was taken down to dryness in vacuo and the residue codistilled with ethanol (200 ml). The residue was crystallized from ethanol (ether added to turbidity) to give 1-(R)-(2-hydroxypropyl) cytosine (2.5 g, 15 mmol, 94%), m.p.246° C. For $C_7H_{11}N_3O_2$ (169,2) calculated: C, 49.69; H, 6.55; N, 24.84. found: C, 49.48; H, 6.70; N, 24.70. $^1$H-NHR-Spectrum (500 MHz, d6-DMSO): H-5: d, 1H, 5.61 ($J_{5,6}$=7.3); H-6: d, 1H, 7,45 ($J_{5,6}$ =7.3); NH2: 2×br s, 2×1H, 7.04 and 6.98; OH: br, 1H, 4.88; 1'-$CH_2$: dd, 1H, 3.73 ($J_{1',2'}$=3.9, $J_{gem}$=13.2) and dd, 1H, 3.31 ($J_{1'',2'}$=8.05, $J_{gem}$=13.2); 2'-CH: m, 1H, 3.82 (J=31.0); 3'-$CH_3$: d, 3H, 1.08 ($J_{3',2'}$=6.35). $[\alpha]_D$=−107.0° (c=0.5, 0.1M HCl).

EXAMPLE 10

1-(R)-(2-Hydroxypropyl)cytosine

To a slurry of sodium hydride (4 g, 0.1 mol, 60% suspension) in distilled dimethylformamide (300 ml) was added under stirring 4-methoxy-2-pyrimidone (12.6 g, 0.1 mol) and the mixture stirred for 1 hour under exclusion of moisture (calcium chloride protection tube). The resulting clear solution was treated with (R)-2-O-tetrahydropyrany-1-O-p-toluenesulfonylpropane-1,2-diol (31.4 g, 0.1 mol) and the reaction mixture heated at 80° C. for 8 hours under stirring. The solvent was then removed in vacuo and the residue triturated with boiling chloroform (three 200-ml-portions) and filtered. The filtrate was purified by silica chromatography to afford 1-(R)-(2-O-tetrahydropyranyloxypropyl)-4-methoxy-2-pyrimidone (16.9 g, 63 mmol, 63%) as an amorphous foam.

This product was heated with methanolic ammonia (500 ml, saturated at 0° C.) in a steel autoclave at 110° C. for 8 hours, cooled and the suspension evaporated in vacuo. The residue was dissolved in 0.25 M sulfuric (300 ml) acid and the solution warmed at 70° C. for 5 hours. The mixture was neutralized with aqueous ammonia, filtered through a layer of Celite 521 (Janssen) and the filtrate concentrated in vacuo. The resulting solution was applied onto a column of Dowex 50×8 (250 ml, 100–200 mesh) in acid form and the column was eluted with water to the loss of UV-absorption of the eluate. The subsequent elution with diluted (1:10) aqueous ammonia afforded UV-absorbing fraction which was pooled and evaporated in vacuo. Crystallization from ethanol gave 1-(R)-(2-hydroxypropyl)cytosine (7.8 g, 46 mmol, 73%), identical with the product prepared according to Example 9.

EXAMPLE 11

9-(R)-(2-Hydroxypropyl-N$^6$-benzoyladenine

A suspension of 9-(R)-(2-hydroxypropyl)adenine (5.8 g, 30 mmol) in pyridine (160 ml) was treated with chlorotrimethylsilane (26 ml) and the mixture was stirred for one hour. Benzoyl chloride (20 ml) was then added and the mixture stirred for additional 2 hours. The reaction mixture was placed in ice-water bath and ice-cold water (30 ml) and concentrated aqueous ammonia (70 ml) were subsequently added dropwise under stirring over 15 min. The mixture was evaporated in vacuo. The residue was codistilled with ethanol (three 150-ml-portions) and crystallized from boiling water. The crystalline product was collected and recrystallized from ethanol (ether added to turbidity) to afford 9-(R)-(2-hydroxypropyl)-$N^6$-benzoyladenine (7.8 g, 26 mmol, 87%), m.p.227° C. $R_F$ 0.40 (TLC, chloroform-methanol, 4:1). For $C_{15}H_{15}N_5O_2$ (297.3) calc.:C, 60.59; H, 5.09; N, 23.56. found C, 60.73; H, 5.28; N, 23.47. $^1$H-NMR-Spectrum (200 MHz, $d_6$-DMSO): H2,H8: 2×s, 2×1H, 8.73 and 8.42, N—CH$_2$+O—CH: m, 3H, 4.05–4.30; 3-CH$_3$: d, 3H, 1.11 (J=5.6); arom. protons+NH: m, 6H, 7.30–8.10. $[\alpha]_D$=+21.7° (c=0.5, DMF).

EXAMPLE 12

9-(S)-(2-Hydroxypropyl)-N6-benzoyladenine

To a stirred suspension of 9-(S)-(2-hydroxypropyl) adenine (6.8 g, 35 mmol) in pyridine (160 ml) was added chlorotrimethylsilane (26 ml) and the mixture was stirred for 1 hour. Benzoyl chloride (20 ml) was added in one portion, the mixture was stirred for additional 2 hours and cooled in ice-water bath. Ice-cold water (30 ml) and conc. aqueous ammonia (70 ml) were added over 15 minute interval and the mixture stirred for additional 30minutes at 0° C. The solvents were evaporated in vacuo and the residue codistilled with water. After crystallization from water the product was collected and recrystallized from ethanol to afford 9-(S)-(2-hydroxypropyl)-$N^6$-benzoyladenine (4.4 g, 15 mmol, 43%), m.p.230° C. The combined mother liquors were evaporated in vacuo and the residue stirred with ethanol (150 ml) for 30 minutes. The suspension was filtered and the precipitate of inorganic salts washed with ethanol (50 ml) and discarded. The filtrate was taken down to dryness in vacuo and the residue triturated with chloroform (two 150-ml-portions) and filtered. The filtrate was chromatographed on a silica gel column (200 ml) to afford, after crystallization from ethyl acetate (petroleum ether added to turbidity) additional crop of the product. Total yield, 7.4 g (25 mmol, 71.5%). For $C_{15}H_{15}N_5O_2$ (297.3) calc.:C, 60.59; H, 5.09; N, 23.56. found C, 60.63; H, 5.16; N, 23.30. $^1$H-NMR spectrum was identical with that of the (R)-isomer in Example 11. $[\alpha]_D$=−25.2° (c=0.5, 0.1M HCl).

EXAMPLE 13

9-(S)-(2-Hydroxypropyl)-$N^2$-benzoylguanine

Chlorotrimethylsilane (20 ml) was added in one portion to a stirred suspension of 9-(R)-(2-hydroxypropyl)guanine (5.0 g, 24 mmol) in pyridine (130 ml) and, after 1 hour stirring, benzoyl chloride (16 ml) was added in one portion. The mixture was stirred for additional 2 hours, cooled by ice-water bath and ice-water (24 ml) followed by conc. aqueous ammonia (56 ml) were added dropwise over 10 minute interval. The reaction mixture was stirred for additional 30 minutes and evaporated in vacuo. The residue was triturated with mixture of water (200 ml) and ethyl acetate (200 ml), filtered, washed with water, ether and dried in vacuo. 9-(S)-(2-Hydroxypropyl)-$N^2$-benzoylguanine (3.4 g, 11 mmol, 45%) obtained was chromatographically pure: $R_F$ 0.33 (TLC, chloroform-methanol, 4:1). m.p.278° C. For $C_{15}H_{15}N_5O_3$.2H$_2$O (349.4) calc.:C, 51.56; H, 5.49; N, 20.05. found C, 51.48; H, 5.41; N, 20.05. $^1$H-NMR Spectrum (500 MHz, $d_6$-DMSO): NH: 2×br, 2×1H, 12.30 and 11.90; H8: s, 1H, 7.95; OH: d, 1H, 5.05 ($J_{2',OH}$=4.9); 1'-CH$_2$: dd, 1H, 4.05 ($J_{1',2'}$=3.4,$J_{gem}$=12.5) and dd, 1H, 3.96 ($J_{1'',2'}$=7.1,$J_{gem}$=12.5), 2'-CH: br m, 1H, 4.01; 3'-CH$_3$: dd, 3H, 1.09 ($J_{3',2'}$=6.1); arom.protons: m, 2H, 8.05 and m, 3H, 7.50–7.70. $[\alpha]_D$=+28.1° (c=0.5, DMF).

EXAMPLE 14

9-(R)-(2-Hydroxypropyl)-N2-benzoylguanine

The reaction mixture composed of 9-(R)-(2-hydroxypropyl)guanine (2.5 g, 12 mmol), pyridine (65 ml) and chlorotrimethylsilane (10 ml) was stirred in a stoppered flask for 1 hour at ambient temperature and benzoyl chloride (8 ml) was added in one portion. After additional 2 hours stirring the mixture was cooled by ice and ice-water (12 ml) followed by conc. aqueous ammonia (28 ml) were added over 5 minute period. After 30 minutes at 0° C., the solvents were evaporated in vacuo and the residue codistilled with ethanol. Crystallization from 80% aqueous ethanol afforded 9-(R)-(2-hydroxypropyl)-N2-benzoylguanine (2.4 g, 7.6 mmol, 63.5%), m.p. 276° C. For $C_{15}H_{15}N_5O_3$.2H$_2$O (349.4) calc.:C, 51.56; H, 5.49; N, 20.05. found C, 51.28; H, 5.62; N, 20.24. $^1$H-NMR spectrum was identical with that of the (S)-isomer (Example 13). $R_F$ 0.33 (TLC, chloroform-methanol, 4:1). $[\alpha]_D$=−28.4° (c=0.5, DMF).

II. Synthesis of Intermediates of the Formula XVII

EXAMPLE 15

(S)-2-(Di(2-propyl)phosphonylmethoxy)-1-(p-toluenesulfonyloxy)propane

To a suspension of sodium hydride (17.2 g, 60% dispersion in oil, 0.43 mol) in dimethylformamide (400 ml) placed in a 1 l round-bottom flask with dropping funnel and calcium chloride protecting tube was under stirring and cooling with ice added dropwise over 30 minutes (S)-2-O-tetrahydropyrany-1,2-propanediol (69.2 g, 0.43 mol). The suspension was stirred for additional 1 hour at 0° C. and benzyl bromide (51 ml, 0.43 mol) was added dropwise at 0° C. The mixture was stirred for 4 hours at 0° C. and left to stand for 48 hours at ambient temperature. Methanolic ammonia (30% solution, 20 ml) was added and, after standing for 2 hours, the solvent was taken down in vacuo. Ethyl acetate (500 ml) was added and the mixture washed with water (four 100-ml-portions). The organic phase was evaporated and the resulting oil in 70% aqueous methanol (400 ml) was stirred under reflux with 50 ml Dowex 50×8 (acid form) for 4 hours. The warm mixture was filtered, washed with methanol and the filtrate evaporated in vacuo. The residual oil was taken in ether (200 ml), washed with water (50 ml), dried and distilled in vacuo. Yield, 60.8 g (85%, b.p. 100–105° C./20 Pa) (S)-1-O-benzyl-1,2-propanediol, $[\alpha]_D$=−13.6° (c=0.5, CHCl$_3$).

This material (0.37 mol) in 1,2-dichlorethane (200 ml) was stirred with paraformaldehyde (20 g) and calcium chloride (10 g) under simultaneous introduction of dry hydrogen chloride for 2 hours at 0° C. The mixture was taken down in vacuo, the residue codistilled with toluene (three 50-ml-portions) and tri(2-propyl)phosphite (50 g) was added. The mixture was heated under stirring to 110° C. and the evolved volatile material distilled off. After the exothermic reaction has subsided, the mixture was heated up to 150° C. and finally the volatiles distilled off at 140° C./1 kPa. The resulting material was filtered through a column (200 ml) of alumina, elution with benzene (0.5 l). The eluate was evaporated and the residue distilled in vacuo to yield (S)-1-benzyloxy-2-[di(2-propyl)phosphonylmethoxy]propane (44 g, 35%, b.p. 125–130° C./13 Pa. For C17H29O5P (344.4) calc.: C,59,28; H,8,49;P,9,01. found C, 59.44; H, 8.28; P, 9.30. Mass-spectrum: Mol.peak 345.1 (M+1).

This product (44 g, 0.128 mol) in methanol (400 ml) was hydrogenated overnight with 10% palladium-on-charcoal (1.5 g, Merck) and conc. hydrochloric acid (0.7 mol) at atmospheric pressure. The mixture was filtered, the filtrate alkalized by the addition of triethylamine and evaporated in vacuo. The residue in ether (200 ml) was washed with water (two 20-ml-portions), dried over magnesium sulfate and evaporated in vacuo to afford (S)-2-(di(2-propyl) phosphonylmethyl)propane-1,2-diol (24.4 g, 75%) as colorless oil.

This residue (24.4 g, 96 mmol) and 4-dimethylaminopyridine (1 g) in pyridine (200 ml) were treated dropwise at 0° C. under stirring with a solution of tosyl chloride (22 g, 0.115 mol) in pyridine (100 ml) and the mixture left to stand at 0° C. overnight. Water (10 ml) was added an the solvent evaporated in vacuo to about half of the original volume. Ethyl acetate (300 ml) was added, the mixture washed successively (100 ml portions) with water, 1M Hcl (to acidic reaction), water, saturated sodium hydrogen carbonate and water. The solution was finally dried with magnesium sulfate and evaporated in vacuo to afford crude product which was purified by chromatography on a column of silica gel (elution by chloroform). (S)-2-[Di(2-propyl) phosphonylmethoxy]-1-p-toluenesulfonyloxypropane was obtained as a thick yellowish oil which was used for further preparations (28 g, 69 mmol).

EXAMPLE 16

(R)-2-[di(2-propyl)phosphonylmethoxy]-1-p-toluenesulfonyloxypropane

The synthesis was performed essentially as described in Example 15 starting with (R)-2-O-tetrahydropyrany-1,2-propanediol (42 g, 0.262 mol). 1-O-Benzyl-(R)-propane-1, 2-diol was obtained by distillation in vacuo (33 g, 76%, b.p. 98–102° C./Pa). $[\alpha]_D$=−12.2° (c=0.5, CHCl$_3$). The chloromethylation and reaction with tri(2-propyl)phosphite gave crude phosphoric acid diester (32 g) which was hydrogenated in methanol (300 ml) with 10% palladium-on-charcoal catalyst (1 g) and hydrochloric acid (0.5 ml) overnight. After work-up according to Example 15 the intermediate afforded (R)-2-[di(2-propyl)phosphonylmethoxy]-1-p-toluenesulfonyloxypropane (24 g, 59 mmol).

III. Synthesis of Products of the Formula I

EXAMPLE 17

9-(R)-(2-Phosphonomethoxypropyl)adenine

A mixture of 9-(R)-(2-hydroxypropyl)-N$^6$-benzoyladenine (3 g, 10 mmol) and di(2-propyl)p-toluenesulfonyloxymethylphosphonate (4.2 g, 12 mmol) was codistilled with dimethylformamide (two 25-ml portions) at 40° C./13 Pa. The residue was redissolved in dimethylformamide (50 ml), cooled by ice and sodium hydride (1.2 g, 30 mmol, 60% dispersion in oil) was added in one portion. The resulting mixture was stirred under calcium chloride protecting tube at ambient temperature for 48 hours. 0.1 M sodium methoxide solution in methanol (150 ml) was added and the mixture set aside overnight under exclusion of moisture. Dowex 50×8 (acid form) was then added to acid reaction of the mixture followed by triethylamine to alkaline reaction of the suspension. After filtration and washing the resin with methanol (200 ml) the filtrate was evaporated to dryness (finally at 40° C./13 Pa). The residue in water (200 ml) was extracted with ether (two 100 ml portions) and the aqueous phase concentrated in vacuo (to approx. 100 ml). This solution was applied onto a Dowex 50×8 column (250 ml) and washed with 20% aqueous methanol until the UV-absorption of the eluate dropped to the original level. The product was then eluted with diluted (1:10) ammonia, pertinent UV-absorbing fractions were pooled and evaporated in vacuo. The residue was codistilled with ethanol (two 50 ml portions) and dried at 13 Pa over phosphorus pentoxide overnight to afford crude di(2-propyl)ester (3 g), $R_F$ =0.55 (TLC chloroform-methanol, 4:1).

Acetonitrile (50 ml) and bromotrimethylsilane (5 ml) were added to this residue and the suspension dissolved by stirring. After standing overnight at ambient temperature in a stoppered flask, the mixture was evaporated in vacuo and water (100 ml) was added to the residue. The mixture was alkified by aqueous ammonia and evaporated in vacuo. The residue dissolved in water was applied on a column of Dowex 50×8 (250 ml, acid form) which was washed with water to the drop of UV-absorption of the eluate followed by elution with aqueous ammonia (1:10) solution. The product containing fraction was evaporated to dryness in vacuo and the residue redissolved in water (50 ml) by alkalization with conc. ammonia to pH 9–9.5. This solution was applied on a column of Dowex 1×2 (250 ml, acetate form) which was then washed with 0.02 M acetic acid to the drop of the UV-absorption of the eluate. The elution was then continued by linear increase of acetic acid concentration (0.02M–1M over 2 liters); the product eluted at 1 M acetic acid. The relevant fractions were pooled, evaporated in vacuo and the residue codistilled with water (three 50-ml-portions). Crystallization from boiling water (three volumes of ethanol added after dissolution) afforded 9-(R)-(2-phosphonomethoxypropyl)adenine (1.35 g, 4.7 mmol, 47%), m.p. 279°. For C$_9$H$_{14}$N$_5$O$_4$P.H$_2$O (305.3) calc.:C, 35.40; H, 5.29; N, 22.94; p, 10.17. found C, 35.28; H, 5.37; N, 23.03; P, 10.17. Electrophoretic mobility (referred to uridine 3'-phosphate): E$_{Up}$=0.80 (in 0.05 M triethylammonium hydrogen carbonate, pH 7.5; 20V/cm). $^1$H-NMR spectrum (200 Mhz, D$_2$O+NaOD): H2: s, 1H, 8.25; H8: s, 1H, 8.09; 1'-CH$_2$: dd, 1H, 4.35 (J$_{1',2'}$=4.4; J$_{gem}$=14.4) and dd, 1H, 4.22 (J$_{1'',2'}$=5.1, J$_{gem}$=14.4); 2'-CH: m, 1H, 3.97 (J=28.4); 3'-CH$_3$: d,3H, 1.11 (J$_{3',2'}$=6.3); P—CH$_2$: dd, 1H, 3.57 (J$_{P,CH}$=9.5,J$_{gem}$=12.4) and dd, 1H, 3.46 (J$_{P,CH}$=9.3,J$_{gem}$= 12.4). $[\alpha]_D$=+21.2° (c=0.5, 0.1M HCl).

EXAMPLE 18

9-(S)-(2-Phosphonomethoxypropyl)adenine

A solution of 9-(S)-(2-hydroxypropyl)-N$^6$-benzoyladenine (3.57 g, 12 mmol) and di(2-propyl)p-toluenesulfonyloxymethylphosphonate (5.25 g, 15 mmol) in dimethylformamide (50 ml) was cooled to −20° C. and sodium hydride (1.44 g, 36 mmol) as 60% dispersion on oil was added in one portion. The mixture was stirred at 0° C. for 3 hours and 48 hours at room temperature under protection against moisture. Further work-up of the reaction mixture was performed as described in Example 17. After purification by chromatography on the column of Dowex 1×2 the product was crystallized from water-ethanol to give 9-(S)-(2-phosphonomethoxypropyl)adenine (1.9 g, 6.7 mmol, 56%). M.p. 276–278° C. For C$_9$H$_{14}$N$_5$O$_4$P.H$_2$O (305.3) calc.:C, 35.40; H, 5.29; N, 22.94; p, 10.17. found C, 35.33; H, 5.56; N, 23.14; P, 10.00. Electrophoretic mobility and $^1$H-NMR spectrum are identical with those of the (R)-isomer (Example 17). $[\alpha]_D=-21.2°$ (c=0.5, 0.1M HCl).

EXAMPLE 19

9-(R)-2-Phosphonomethoxypropyl)-2,6-diaminopurine 9-(R)-(2-Hydroxypropyl)-2,6-diaminopurine (2.1 g, 10 mmol) was dissolved by warming in a mixture of dimethylformamide (40 ml) and dimethylformamide dimethylacetal (25 ml) and the solution was left to stand aside in a stoppered flask overnight. The mixture was evaporated at 40° C./13 Pa and codistilled with dimethylformamide (two 20-ml-portions). 50% aqueous pyridine (50 ml) was added to the residue followed up by dry ice, the mixture was evaporated at 40° C./13 Pa, codistilled with pyridine (four 25-ml-portions) and di(2-propyl)p-toluenesulfonyloxymethylphosphonate (4.2 g, 12 mmol) was added to the residue. The mixture was then codistilled with dimethylformamide (two 25-ml-portions), redissolved in the same solvent (40 ml) and cooled down to –10° C. Sodium hydride (1.2 g, 30 mmol) as 60% suspension in oil was added in one portion and the mixture stirred at 0° C. for 3 hours and 48 hours at room temperature under protection against moisture. Acetic acid (1.8 ml, 30 mmol) was added, the mixture was evaporated at 40° C./13 Pa to dryness. The residue was dissolved in diluted (1:1) aqueous ammonia, (100 ml), left to stand overnight and evaporated to dryness in vacuo. The residue was deionized on the column of Dowex 50×8 (200 ml) as described in Example 15 and the ammonia eluate dried at 13 Pa over phosphorus pentoxide overnight.

Acetonitrile (30 ml) and bromotrimethylsilane (3 ml) were added and the mixture homogenized by gentle shaking in a stoppered flask. The solution was left to stand overnight and evaporated in vacuo. The residue was dissolved in water (100 ml) and, after 30 minutes standing the solution was alkalified by ammonia and evaporated. This residue was deionized on a Dowex 50×8 column (200 ml, acid form) as described in Example 17. The residue of ammonium salt was dissolved in water (50 ml) by addition of ammonia to pH 9–9.5 and this solution was applied on a column (200 ml) of Sephadex A-25 in hydrogen carbonate form, equilibrated by 0.02 M triethylammonium hydrogen carbonate. The column was first eluted by the equilibration buffer to the drop of UV-absorption and then by linear gradient of triethylammonium hydrogen carbonate (pH 7.5) (formed from 0.02 M and 0.3 M buffer, 1 l each). The product eluted at 0.10–0.15 M concentration, the relevant fractions were pooled, evaporated in vacuo and the residue coevaporated with methanol (three 50-ml-portions). The residue dissolved in water (25 ml) was applied on a column (50 ml) of Dowex 1×2 (acetate) which was first washed with water to the disappearance of UV-absorption. The resin was transferred to a 300 ml beaker and stirred with 1M acetic acid (200 ml). The suspension was filtered and the resin washed with boiling water (1 liter). The combined filtrate was evaporated in vacuo and the residue codistilled with water (three 50-ml-portions). The residue was dissolved in boiling water (100 ml), filtered while hot and ethanol (150 ml) added to the filtrate. The product which crystallized on ice-cooling was collected by filtration, washed with ethanol, ether and dried in vacuo. 9-(R)-(2-Phosphonomethoxypropyl)-2,6-diaminopurine (1.4 g, 4.7 mmol, 47%) was obtained as a free acid, m.p. 287° C. For $C_9H_{15}N_6 O_4P.H_2O$ (302.3) calc.:C, 35.75; H, 5.00; N, 27.80; P, 10.27. found C, 35.93; H, 5.02; N, 27.59; P, 10.28. $^1$H-NMR-Spectrum (500 MHz, $D_2O$+NaOD): H8: s, 1H, 7.94: 1'-$CH_2$: dd, 1H, 4.7 ($J_{1',2'}$=4.4) and dd, 1H, 4.09 ($J_{1'',2'}$==5.4, $J_{gem}$=14.65); 2'-CH: m, 1H, 3.93 (J=28.8); 3'-$CH_3$: d, 3H, 1.12 ($J_{CH3,CH}$=6.3); P—$CH_2$: dd, 1H, 3.54, ($J_{P,CH}$=9.3, $J_{gem}$=12.2) and dd, 1H, 3.45 ($J_{P,CH}$=9.3,$J_{gem}$=12.2): Electrophor.mobility:$E_{UP}$=0.70. $[\alpha]_D=-26.1°$ (c=0.5, 0.1M HCl).

EXAMPLE 20

9-(S)-(2-Phosphonomethoxypropyl)-2.6-diaminopurine

This compound was prepared from 9-(S)-(2-hydroxypropyl)-2,6-diaminopurine (2.1 g, 10 mmol) essentially as described in Example 19 for its (R)-enantiomer. The yield of 9-(S)-(2-phosphonomethoxypropyl)-2,6-diaminopurine crystallized as free acid from water-ethanol amounted to 33% (1.0 g, 3.3 mmol). M.p. 275–278° C. For $C_9H_{15}.N_6O_4P.H_2O$ (302.3) calc.:C, 35.75; H, 5.00; N, 27.80; P, 10.27. found C, 35.56; H, 5.08; N, 27.99; P, 10.18. Electrophoretic mobility: $E_{Up}$=0.70; $^1$H-NMR spectrum is identical with that of its (R)-enantiomer (Example 19). $[\alpha]_D=+28.5°$ (c=0.5, 0.1M HCl).

EXAMPLE 21

9-(R)-(2-Phosphonomethoxypropyl)quanine

A mixture of 9-(R)-(2-hydroxypropyl)-$N^2$-benzoylguanine (2.5 g, 7 mmol) and di(2-propyl)p-toluenesulfonyloxymethylphosphonate (2.9 g, 8.4 mmol) was codistilled with dimethylformamide (two 25-ml-portions) at 40° C./13 Pa and the residue redissolved in dimethylformamide (30 ml). Sodium hydride (0.84 g, 21 mmol) in 60% dispersion in oil was added at one portion and the mixture stirred for 24 hours at room temperature under the exclusion of moisture. Methanol (100 ml) was added to the mixture which was then left to stand overnight, neutralized with Dowex 50×8 (acid form) and filtered. The filtrate was evaporated to dryness in high vacuum and the residue in water (150 ml) extracted with ether (two 50-ml-portions). The aqueous solution was concentrated in vacuo to approx. 50 ml and applied on a column of Dowex 50×8 (150 ml) (acid form) which was first washed with water to the drop of UV-absorption and then with diluted (1:10) ammonia. The ammonia fraction was evaporated, the residue codistilled with ethanol (two 50-ml-portions) and finally dried overnight at 13 Pa over phosphorus pentoxide.

Acetonitrile (40 ml) and bromotrimethylsilane (4 ml) were added to the residue and the mixture dissolved by stirring in a stoppered flask. After standing overnight at ambient temperature, the mixture was evaporated in vacuo and the residue dissolved in water (100 ml). After 30 minutes, the solution was alkalized with ammonia and evaporated. The deionization and purification on Dowex 1×2 were performed essentially as described in Example 17. The final purified free acid form of 9-(R)-(2-phosphonomethoxypropyl)guanine was precipitated from ethanol with ether to give 0.90 g (3 mmol, 43%) of the material with m.p. 286° C. For $C_9H_{14}N_5O_5P$ (303.3) calc.:C, 35.64; H, 4.65; N, 23.10; P, 10.23. found C, 35.35; H, 4.58; N, 23.24; P, 10.40. $[\alpha]_D=-26.1°$ (c=0.5, 0.1M HCl). $^1$H-NMR-Spectrum (500 MHz, $D_2O$, NaOD): H-8: s, 1H, 7.90; 1'-$CH_2$: dd, 1H, 4.21 ($J_{1',2'}$=4.6, $J_{gem}$=14.5) and dd, 1H, 4.15 ($J_{1'',2'}$=5.5, $J_{gem}$=14.5); 2'-CH: m, 1H, 3.99 (ΣJ=28.7); 3'-$CH_3$: d, 3H, 1.14 ($J_{3',2'}$=6.2); P—$CH_2$: dd, 1H, 3.56 ($J_{P,CH}$=9.3, $J_{gem}$=12.4) and dd, 1H, 3.48 ($J_{P,CH}$=9.2, $J_{gem}$=12.4).

EXAMPLE 22

9-(S)-(2-Phosphonomethoxypropyl)guanine

A mixture of 9-(S)-(2-hydroxypropyl)guanine (1.57 g, 5 mmol) and di(2-propyl)p-toluenesulfonyloxymethylphosphonate (2.1 g, 6 mmol) was codistilled with dimethylformamide (two 20-ml-portions) at 40° C./13 Pa and the residue redissolved in dimethylformamide (20 ml). Sodium hydride (0.6 g, 15 mmol)) as 60% dispersion in oil was added in one portion and the mixture stirred for three days at room temperature under exclusion of moisture. Methanol (30 ml) was added and the solution left to stand overnight. After neutralization with Dowex 50×8 (acid form) and filtration, the filtrate was evaporated to dryness in vacuo and the residue deionized as described in Example 17. The ammonia eluate of the crude diester was dried at 13 Pa over phosphorus pentoxide. Acetonitrile (30 ml) and bromotrimethylsilane (3 ml) were added and the mixture dissolved by stirring. After standing overnight at room temperature, the reaction mixture was worked up as described in Example 17. 9-(S)-(2-Phosphonomethoxypropyl)guanine was isolated as a free acid similarly as described for its (R)-enantiomer (Example 21) in the 43% yield (0.65 g, 2.15 mmol). m.p. 287° C. For $C_9H_{14}N_5O_5P$ (303.3) calc.:C, 35.64; H, 4.65; N, 23.10; P, 10.23. found C, 35.72; H, 4.54; N, 23.06; P, 10.29. $^1$H-NMR-Spectrum is identical with that of the (R)-enantiomer. $[\alpha]_D$=+26.3° (c=0.5, 0.1M HCl).

EXAMPLE 23

1-(R)-(2-Phosphonomethoxypropyl)cytosine

The mixture of 1-(R)-(2-hydroxypropyl)cytosine (1.7 g, 10 mmol), dimethylformamide (40 ml) and dimethylformamide dimethylacetal (15 ml) was stirred overnight and evaporated at 40° C./13 Pa. 50% aqueous pyridine (20 ml) and enough dry ice was added to keep its excess for 15 minutes. The mixture was again evaporated and codistilled with pyridine (three 25-ml-portions) at 40°/13 Pa. Di-(2-propyl)p-toluenesulfonyloxyphosphonate (4.2 g, 12 mmol) was added and the mixture codistilled with dimethylformamide (two 25-ml-portions) under the same conditions. The residue in dimethylformamide (40 ml) was treated at –10° C. with sodium hydride (720 mg, 30 mmol) and the mixture stirred at ambient temperature for 48 hours under exclusion of moisture. 0.1 M Sodium methoxide in methanol (100 ml) was added and, after standing overnight, the mixture was neutralized with Dowex 50×8 (acid form). The suspension was filtered, evaporated to dryness in vacuo and the residue deionized on a column of Dowex 50×8 (acid form, 150 ml). The ammonia eluate was evaporated, dried in vacuo over phosphorus pentoxide and the residue treated with bromotrimethylsilane (3 ml) and acetonitrile (30 ml) overnight. After evaporation in vacuo, the residue was treated with water (50 ml), alkalized with ammonia and evaporated in vacuo. The residue was deionized on a column of Dowex 50×8 (see above) and the crude material purified by anion exchange chromatography on Dowex 1×2 (acetate) column (100 ml) with a linear gradient of acetic acid (composed of 1 l water and 1 l 0.3 M acetic acid). The product fraction was evaporated, codistilled with water (three 30-ml-portions) and 1-(R)-(2-phosphonomethoxypropyl)cytosine (0.90 g, 19%) obtained by crystallization from water-ethanol. M.p. 261° C. $E_{Up}$=0.70. For $C_8H_{14}N_3O_5P$ (263.3) calc.: C, 36.50; H, 5.36; N, 15.97; P, 11.79. found C, 36.43; H, 5.39; N, 16.05; P, 11.82. $[\alpha]_D$=–108.10° (c=0.5, 0.1M HCl).

EXAMPLE 24

9-(S)-(2-Phosphonomethoxypropyl)adenine

A mixture of adenine (1.62 g, 12 mmol) and cesium carbonate (2.1 g, 6.5 mmol) in dimethylformamide was stirred at 100° C. and a solution of (S)-2-[(di(2-propyl)phosphonylmethoxy]-1-toluenesulfonyloxypropane (4.1 g, 10 mmol) in dimethylformamide (10 ml) was added in one portion. The mixture was heated at 110° C. under stirring with exclusion of moisture for 8 hours and evaporated in vacuo. The residue was triturated with boiling chloroform (three 50-ml-portions), filtered and evaporated in vacuo. The crude material afforded on purification by silica gel chromatography (150 ml) di-(2-propyl) (S)-9-(2-phosphonomethoxypropyl)adenine which crystallized from ether (1.7 g, 46%), m.p. 97–98° C. For $C_{15}H_{26}N_5O_4P$ (371.5) calc.: C, 48.50; H, 7.06; N, 18.86; P, 8.36. found C, 48.27; H, 7.15; N, 18.85; P, 8.44. $[\alpha]_D$=+2.80 (c=0.5, DMF).

This product (1.4 g, 3.9 mmol) in acetonitrile (25 ml) was treated with bromotrimethylsilane (2.5 ml) overnight at room temperature. The mixture was taken down in vacuo and the product desalted and purified by chromatography on Dowex 1×2 column (100 ml) as described in Example 17. Yield, 76%, m.p. 277–278° C. $[\alpha]_D$=+21.7.

EXAMPLE 25

9-(R)-(2-Phosphonomethoxypropyl)adenine

The reaction was performed with 12 mmol adenine and 10 mmol (R)-2-[(di(2-propyl)phosphonylmethoxy]-1-toluenesulfonyloxypropane according to Example 22. Di(2-propyl) (R)-9-(2-phosphonomethoxypropyl)adenine m.p. 97° C. was obtained by chromatography on silica gel and crystallized from ether (2.8 g, 75.5%). For $C_{15}H_{26}N_5O_4P$ (371.5) calc.: C, 48.50; H, 7.06; N, 18.86; P, 8.36. found C, 48.78; H, 7.22; N, 18.77; P, 8.23. $[\alpha]_D$=–2.9° (c=0.5, DMF). The reaction of this product (1.8 g, 4.9 mmol) with bromotrimethylsilane (3 ml) and acetonitrile (30 ml) was performed as described in Example 22. Yield, 80% of 9-(R)-(2-phosphonomethoxypropyl)adenine. $[\alpha]_D$=21.5°, m.p. 279° C.

EXAMPLE 26

9-(R)-(2-Phosphonomethoxypropyl)-2-aminopurine

Sodium hydride (1.4 g, 60% dispersion, 35 mmol) was added to a stirred solution of 2-amino-6-chloropurine (5.94 g, 35 mmol) in dimethylformamide (60 ml) and after 1 hour stirring at ambient temperature (R)-2-[di(2-propyl)phosphonylmethoxy]-1-p-toluenesulfonyloxypropane (12.2 g, 30 mmol) in dimethylformamide (20 l) was added in one portion. The mixture was stirred at 80° C. for 10 hours and evaporated in vacuo. The residue was extracted with boiling chloroform (300 ml), filtered and the filtrate was evaporated in vacuo. The residue afforded by silica gel column chromatography (elution with chloroform-methanol mixture, 95:5) di(2-propyl) 9-(R)-(2-phosphonomethoxypropyl)-2-amino-6-chloropurine (7.5 g, 53%) as a thick oil, $R_F$ 0.55 (TLC on silica gel in chloroform-methanol, 9:1).

A solution of this diester (2.5 g, 6.2 mmol) in 200 ml methanol and 0.5 ml conc. hydrochloric acid was hydrogenated over 10% Pd/C catalyst (1 g) at room temperature overnight, the mixture was filtered, filtrate alkalized with triethylamine and evaporated in vacuo. The residue was deionized on Dowex 50×8 (acid form) (100 ml) as described in Example 24 and the ammonia eluate evaporated and dried in vacuo over phosphorus pentoxide. Acetonitrile (25 ml) and bromotrimethylsilane (2.5 ml) was added and the solution left to stand overnight at room temperature. The mixture was evaporated to dryness and the residue taken up in water (25 ml). After 30 min the solution was alkalized with ammonia and evaporated. The residue afforded on deionization on Dowex 1×2 (acetate) (150 ml) with linear gradient of acetic acid (0.75 l water, 0.75 l 0.5 M acetic acid) product which was isolated from the pooled fractions by crystallization from water-ethanol (1:1). Yield, 0.62 g (35.5%) of 9-(R)-(2-phosphonomethoxypropyl)-2-aminopurine, m.p. 156° C. For $C_9H_{14}N_5O_4P$ (287.3) calc.: C, 37.62; H, 4.91; N, 24.38; P, 10.80. found: C, 37.42; H, 5.05; N, 24.65; P, 11.06.

EXAMPLE 27

9-(R)-(2-Phosphonomethoxypropyl)-2-amino-6-thiopurine

A solution of di(2-propyl)-9-(R)-(2-phosphonomethoxypropyl)-2-amino-6-chloropurine (2.5 g, 6.2 mmol) (prepared according to Example 26), thiourea (2.0 g) and absolute ethanol (100 ml) was stirred in reflux for one hour, alkalized with triethylamine and evaporated. The residue was extracted with chloroform (2×100 ml), filtered and the filtrate taken down to dryness and evaporated in vacuo. The residue ($R_F$ 0.40, TLC on silica gel, chloroform-methanol, 4:1) was dried over phosphorus pentoxide overnight and treated with acetonitrile (30 ml) and bromotrimethylsilane (3 ml). After standing overnight at room temperature, the mixture was evaporated to dryness and taken down in water (50 ml). After 30 min it was alkalized with ammonia, evaporated in vacuo and the residue deionized on Dowex 50 (cf. Example 25). The ammonia eluate was taken down in vacuo and applied on a column of Dowex 1×2 (acetate) (150 ml) which was washed first with water and with 1 M acetic acid (500 ml each). These eluates were discarded, the resin was stirred with 2 M formic acid (500 ml), filtered and washed with boiling water (total, 1 l). The filtrate was evaporated to dryness, the residue codistilled with water (3×50 ml) and crystallized from water (equal volume of ethanol added after dissolution). Yield, 1.0 g (50%) 9-(R)-(2-phosphonomethoxypropyl)-2-amino-6-thiopurine, m.p. 188° C. (dec.). For $C_9H_{14}N_5O_4P$ (319.3) calc.: C, 33.85; H, 4.42; N, 21.94; P, 9.72; S, 10.04. found: C, 33.83; H, 4.69; N, 22.15; P, 9.99; S, 10.30.

EXAMPLE 28

9-(R)-(2-phosphonomethoxypropyl)-2-amino-6-azidopurine

A solution of di(2)-propyl) 9-(R)-(2-phosphonomethoxypropyl)-2-amino-6-chloropurine (2.5 g, 6.2 mmol) (prepared according to Example 26) and lithium azide (1.0 g) in dimethylformamide (40 ml) was stirred 4 hours at 100° C. under exclusion of moisture, filtered over Celite, washed with dimethylformamide (20 ml) and the filtrate evaporated in vacuo. The residue ($R_F$ 0.30, TLC on silica gel, chloroform-methanol, 9:1) was dried over phosphorus pentoxide overnight and treated with acetonitrile (20 ml) and bromotrimethylsilane (2 ml). After standing overnight at room temperature, the mixture was evaporated to dryness and taken down in water (50 ml) After 30 min it was alkalized with ammonia, evaporated in vacuo and the residue applied on Dowex 50 (acid form) column (100 ml). Washing with water eluted with retention the UV-absorbing peak of the product which was evaporated in vacuo and the residue crystallized from water (equal volume of ethanol added after dissolution. Yield, 0.95 g (47%) 9-(R)-(2-phosphonomethoxypropyl)-2-amino-6-azidopurine, not melting to 300° C. For $C_9H_{13}N_8O_4P$ (328.3) calc.: C, 32.92; H, 3.99; N, 34.14; P, 9.45. found: C, 233.03; H, 4.29; N, 33.75; P, 9.59.

EXAMPLE 29

9-(R)-(2-Phosphonomethoxypropyl)-2,6-diaminopurine 9-(R)-(2-phosphonomethoxypropyl)-2-amino-6-azidopurine (0.30 g, prepared according to Example 27) in 50% aqueous methanol (200 ml) containing hydrochloric acid (0.5 ml) was hydrogenated over 10% Pd/C (0.5 g) overnight at room temperature. The mixture was filtered, washed with water, filtrate alkalized with ammonia and evaporated in vacuo. The residue was deionized on a column of Dowex 50×8 (50 ml) (cf. Example 25) and the ammonia eluate evaporated to dryness. The residue in water (pH adjusted to 9) was applied on a column of Dowex 1×2 (acetate) which was first washed with water to remove salts and the product was then eluted with 1 M acetic acid. The fractions containing product were pooled, evaporated to dryness and codistilled with water (3×20 ml). The residue was crystallized from water (ethanol added to turbidity) to afford 9-(R)-(2-phosphonomethoxypropyl)-2,6-diaminopurine (120 mg) identical with the preparation according to Example 19.

EXAMPLE 30

9-(R)-(2-Phosphonomethoxypropyl)-3-deazaadenine

A mixture of 3-deazaadenine (1.45 g, 10.8 mmol), cesium carbonate (1.75 g, 5.4 mmol) and dimethylformamide (25 ml) was stirred at 100° C. for 1 h and a solution of (R)-2-[di(2-propyl)phosphonylmethoxy]-1-p-toluenesulfonyloxypropane (3.67 g, 9 mmol) in dimethylformamide (10 ml) was added in one portion. The mixture was then heated for 24 hours at 110° C. under exclusion of moisture and taken down to dryness. The residue was extracted with boiling chloroform (total 300 ml), filtered and the filtrate evaporated. The residue was chromatographed on a column of silica gel (300 ml) in chloroform affording, after crystallization of the relevant fractions from ethyl acetate-petroleum ether, di(2-propyl) 9-(R)-(2-phosphonomethoxypropyl)-3-deazaadenine in the yield of 1.07 g (32.2%), m.p. 122° C. For $C_{16}H_{27}N_4O_4P$ (370.5) calc.: C, 51.87; H, 7.35; N, 15.13; P, 8.38. found: C, 52.03; H, 7.69; N, 15.15, P, 8.59. UV-Spectrum (pH2): $1_{max}$ 262 (ε16500).

This diester (1.0 g, 2.7 mmol) was treated with acetonitrile (25 ml) and bromotrimethylsilane (2.5 ml) overnight. The mixture was then worked up as described in Example 27 to afford, after deionization and chromatography on Dowex 1×2 9-(R)-(2-phosphonomethoxypropyl)-3-deazaadenine in 78% yield, not melting to 300° C. For $C_{10}H_{15}N_4O_4P$ (286.3) calc.: C, 41.95; H, 5.28; N, 19.57; P, 10.84. found: C, 42.03; H, 5.63; N, 19.75; N, 19.75; P, 11.09. UV-Spectrum (pH2): $1_{max}$ 262 (ε16500). $E_{Up}$=0.68 (pH 7.5).

EXAMPLE 31

9-(R)-(2-Phosphonomethoxypropyl)-8-azaadenine and 8-(R)-(2-phosphonomethoxypropyl)-8-azaadenine A mixture of 8-azaadenine (1.45 g, 10.8 mmol), cesium carbonate (1.75 g, 5.4 mmol) and dimethylformamide (25 ml) was preheated to 100° C. and a solution of (R)-2-[di(2-propyl)phosphonylmethoxy]-1-p-toluenesulfonyloxy propane (3.67 g, 9 mmol) in dimethylformamide (10 ml) was added in one portion. The mixture was then heated for 6 hours at 110° C. under exclusion of moisture and taken down to dryness. The residue was extracted with boiling chloroform (total 300 ml), filtered and the filtrate evaporated. The residue was chromatographed on a column of silica gel (300 ml). Elution with chloroform containing 5% methanol afforded di(2-propyl) 9-(R)-(2-phosphonomethoxypropyl)-8-azaadenine as a thick oil in yield of 0.90 g (37%). UV-Spectrum (pH2): $1_{max}$ 265.5 (ϵ14000). $R_F$ 0.50 (TLC on silica gel in chloroform-methanol, 9:1). Further elution with the same solvent afforded di(2-propyl) 8-(R)-2-phosphonomethoxypropyl)-8-azaadenine as semisolid material in the yield of 0.75 g (22%). UV-Spectrum (pH2): $1_{max}$ 284 nm. $R_F$ 0.40 (TLC on silica gel in chloroform-methanol 9:1).

Each fraction was separately treated with acetonitrile (25 ml) and bromotrimethylsilane (2.5 ml) overnight and the mixtures worked up as described in Example 27. Chromatography on Dowex 1×2 column (50 ml) afforded 9-(R)-(2-phosphonomethoxypropyl)-8-azaadenine on elution with 2 M acetic acid. Yield (after crystallization from water-ethanol, 79%. UV-Spectrum (pH2): $1_{max}$ 265 nm (ϵ14000). For $C_8H_{14}N_6O_4P$ (289.3) calc.: C, 33.21; H, 4.88; N, 29.06; P, 10.73. found C, 32.97; H, 4.63; N, 29.00; P, 11.10.

8-(R)-(2-phosphonomethoxypropyl)-8-azaadenine was obtained similarly by elution with 1 M acetic acid. Yield, 72%. UV-Spectrum (pH2): $1_{max}$ 284 nm. For $C_8H_{14}N_4O_4P$ (289.3) calc.: C, 33.21; H, 4.88; N, 29.06; P, 10.73. found: C, 33.45; H, 5.06; N, 29.23; P, 10.66.

EXAMPLE 32

9-(R)-(2-Phosphonomethoxypropyl)hypoxanthine

A solution of 9-(R)-(2-phosphonomethoxypropyl)adenine (400 mg, 1.4 mmol) and sodium nitrite (1.4 g, 20 mmol) in water (40 ml) was cooled in an ice bath and conc. hydrochloric acid (2 ml) was added. The mixture was stirred in an argon atmosphere at 0° C. for 3 h and then overnight at an ambient temperature. The mixture was applied onto a column (100 ml) Dowex 50×8 (acid form) and the column eluted with water. The product was eluted with retention; the pertinent fraction was evaporated in vacuo, the residue codistilled with ethanol (2×50 ml) and the crystalline residue filtered with ether. Yield, 250 mg (62%) 9-(R)-(2-phosphonomethoxypropyl)hypoxanthine, UV-Spectrum (pH2): $1_{max}$ 251 nm. For $C_9H_{13}N_4O_5P$ (288.3) calc.: C, 37.50; N, 4.54; N, 19.44; P, 10.77. found: C, 37.35; H, 4.55; N, 19.22; P, 10.86.

EXAMPLE 33

9-(S)-(2-Phosphonomethoxypropyl)hypoxanthine

A solution of 9-(S)-phosphonomethoxypropyl)adenine (400 mg, 1.4 mmol) and sodium nitrite (1.4 g, 20 mmol) in water (40 ml) was cooled in an ice bath and conc. hydrochloric acid (2 ml) was added. Further work-up of the reaction was performed as described in Example 31. Yield, 66% 9-(S)-(2-phosphonomethoxypropyl)hypoxanthine. UV-Spectrum (pH2): $1_{max}$ 251 nm. For $C_9H_{13}N_4O_5P$ (288.3) calc.: C, 37.50; H, 4.54; N, 19.44; P, 10.77. found: C, 37.80; H, 4.65; N, 19.56; P, 10.55.

EXAMPLE 34

9-(R)-(2-Phosphonomethoxypropyl)-2-amino-6-dimethylaminopurine

A solution of di(2-propyl) 9-(R)-(2-phosphonomethoxypropyl)-2-amino-6-chloropurine (0.50 g, prepared according to Example 26) in 20% dimethylamine in methanol is heated to 110° C. for 20 h in a pressure vessel and the solution evaporated in vacuo. The residue in 50% aqueous methanol (20 ml) is applied onto a column (50 ml) of Dowex 50×8 ($H^+$-form) in 20% aqueous methanol and the column washed with the same eluent until the UV-absorption dropped to the original value. The column is then washed with 2.5% ammonia solution in 20% aqueous methanol and the UV-absorbing eluate taken to dryness, codistilled twice with ethanol (25 ml each) and dried over phosphorus pentoxide at 13 Pa. The resulting product is treated with acetonitrile (30 ml) and bromotrimethylsilane (3 ml) overnight at room temperature and the solution evaporated in vacuo. Water (50 ml) is added, the mixture alkalized by addition of conc. aqueous ammonia and the solution evaporated. Further work-up and purification is performed essentially as described in Example 17. Yield, 0.40 g (95%) 9-(R)-(2-phosphonomethoxypropyl)-2-amino-6-dimethylaminopurine, m.p. 154–156° C., $[\alpha]_D=-10.6°$ (c=0.5, 0.1M HCl). $^1$H-NMR spectrum ($D_2O$+NaOD): 1.165 d(3H), $J_{3',2'}$=6.3 $CH_3$; 3.27 s (6H) N—$CH_3$; 3.47 dd(1H), $J_{P,CH}$=9.5, $J_g$=12.9 and 3.65 dd(1H) $J_{P,CH}$=9.3, $J_g$=12.9, P—$CH_2$; 3.91 m, ΣJ=29.0 2'-CH; 4.06 dd(1H), $J_{1'',2'}$=6.4, $J_g$=14.16 and 4.16 dd(1H), $J_{1'2'}$=3.7, $J_g$=14.16 1'-$CH_2$; 7.79 s(1H), H-8. For $C_{11}H_{19}N_6O_4P$ (330.3) calc. C, 40.00; H, 5.80; N, 25.44; P, 9.38. found C, 39.54; H, 5.75; N, 24.78; P, 8.92.

EXAMPLE 35

9-(R)-(2-Phosphonomethoxypropyl)-2-amino-6-diethylaminopurine

A mixture of di(2-propyl) 9-(R)-(2-phosphonomethoxypropyl)-2-amino-6-chloropurine (0.50 g, prepared according to Example 26) and diethylamine (2 ml) in methanol (20 ml) is heated to 100° C. for 20 h in a pressure vessel and the solution evaporated in vacuo. The residue in 50% aqueous methanol (20 ml) is applied onto a column (50 ml) of Dowex 50×8 ($H^+$-form) in 20% aqueous methanol and the column is washed with the same eluent until the UV-absorption dropped to the original value. The column is then washed with 2.5% ammonia solution in 20% aqueous methanol and the UV-absorbing eluate taken to dryness, codistilled twice with ethanol (25 ml each) and dried over phosphorus pentoxide at 13 Pa. The resulting product is treated with acetonitrile (30 ml) and bromotrimethylsilane (3 ml) overnight at room temperature and the solution evaporated in vacuo. Water (50 ml) is added, the mixture alkalized by addition of conc. aqueous ammonia and the solution evaporated. Further work-up and purification is performed essentially as described in Example 17. Yield, 0.40 g (95%) 9-(R)-(2-phosphonomethoxypropyl)-2-amino-6-diethylaminopurine, m.p.162–164° C., $[\alpha]_D=-9.8°$ (c=0.5, 0.1M HCl). For $C_{13}H_{23}N_6O_4P$ (358.4) calc. C, 43.56; H, 6.47; N, 23,45; P, 8.66. found C, 43.80; H, 6.73; N, 23.78; P, 8.90.

EXAMPLE 36

9-(R)-(2-Phosphonomethoxypropyl)-2-amino-6-butylaminopurine

A mixture of di(2-propyl) 9-(R)-(2-phosphonomethoxypropyl)-2-amino-6-chloropurine (0.50 g, prepared according to Example 26), butylamine (2.0 ml) and ethanol (20 ml) is refluxed under exclusion of moisture for 6 h and evaporated in vacuo. The work-up of the reaction mixture, following reaction with bromotrimethylsilane and isolation of the product is performed essentially as described in Example 34. Yield, 0.40 g (87%) of 9-(R)-(2-phosphonomethoxypropyl)-2-amino-6-butylaminopurine, m.p.140–142° C., $[\alpha]_D=-11.9°$ (c=0.5, 0.1M HCl). $^1$H-NMR spectrum (D$_2$O+NaOD):1.18 d(3H), $J_{3',2'}$=5.9 CH$_3$; 3.52 dd(1H), $J_{P,CH}$=9.8, $J_g$=12.5 and 3.67 dd(1H) $J_{P,CH}$=9.5, $J_g$=12.5, P—CH$_2$; 3.93 m, 2'-CH; 4.05 dd(1H), $J_{1'',2'}$=6.1, $J_g$=14.6 and 4.16 dd(1H), $J_{1',2'}$=3.5, $J_g$=14.6 1'-CH$_2$; 7.83 s(1H), H-8; butyl: 0.92 t(3H), J=7.3 CH$_3$; 1.38 br sext(2H), ΣJ=36.6 3-CH$_2$; 1.59 br pent(2H), ΣJ=28.3 2-CH$_2$; 3.43 br m(2H) 1-CH$_2$. For C$_{13}$H$_{24}$N$_6$O$_4$ P (359.4) calc. C, 43.44; H, 6.73; N, 23.39; P, 8.64. found C, 43.31; H, 6.20; N, 23.57; P, 8.90.

EXAMPLE 37

9-(R)-(2-Phosphonomethoxypropyl)-2-amino-6-(2-butyl)aminopurine

A mixture of di(2-propyl) 9-(R)-(2-phosphonomethoxypropyl)-2-amino-6-chloropurine (0.50 g, prepared according to Example 26), 2-butylamine (2.0 ml) and ethanol (20 ml) is refluxed under exclusion of moisture for 8 h and evaporated in vacuo. The work-up of the reaction mixture, following reaction with bromotrimethylsilane and isolation of the product is performed essentially as described in Example 34. Yield, 0.35 g (75%) of 9-(R)-(2-phosphonomethoxypropyl)-2-amino-6-(2-butyl)aminopurine, m.p.148–149° C., $[\alpha]_D=-14.5°$ (c=0.5, 0.1M HCl). $^1$H-NMR spectrum (D$_2$O+NaOD): 1.17 d(3H), $J_{3',2'}$=6.3, CH$_3$; 3.51 dd(1H), $J_{P,CH}$=9.5, $J_g$=12.5 and 3.63 dd (1H) $J_{P,CH}$=9.3, $J_g$=12.5, P—CH$_2$; 3.94 m, 2'-CH; 4.08 dd(1M), $J_{1'',2'}$=6.1, $J_g$=14.6 and 4.19 dd(1H), $J_{1',2'}$=3.5, $J_g$=14.6 1'-CH$_2$; 7.88 s(1H), H-8; 2-butyl: 0.94 t(3H), J=7.3+1.25 d(3H), J=6.6 CH$_3$; 1.61 br pent(2H), ΣJ=28.1 CH$_2$; 4.15 br m(1H) CH. For C$_{13}$H$_{24}$N$_6$O$_4$P (359.4) calc. C, 43.44; H, 6.73; N, 23.39; P, 8.64. found C, 43.35; H, 6.59; N, 23.67; P, 8.68.

EXAMPLE 38

9-(R)-(2-Phosphonomethoxypropyl)-2-amino-6-cyclopropylaminopurine

A mixture of di(2-propyl) 9-(R)-(2-phosphonomethoxypropyl)-2-amino-6-chloropurine (0.50 g, prepared according to Example 26), cyclopropylamine (2.0 ml) and ethanol (20 ml) is refluxed under exclusion of moisture for 12 h and evaporated in vacuo. The work-up of the reaction mixture, following reaction with bromotrimethylsilane and isolation of the product is performed essentially as described in Example 34. Yield, 0.35 g (80%) of 9-(R)-(2-phosphonomethoxypropyl)-2-amino-6-cyclopropylaminopurine, m.p.178–179° C., $[\alpha]_D=-23.5°$ (c=0.5, 0.1M HCl). $^1$H-NMR spectrum (D$_2$O+NaOD):1.21 d(3H), $J_{3',2'}$=6.1 CH$_3$; 3.56 dd(1H), $J_{P,CH}$=9.8, $J_g$=12.9 and 3.73 dd (1H) $J_{P,CH}$=9.8, $J_g$=12.9, P—CH$_2$; 3.96 m, 2'-CH; 4.06 dd(1H), $J_{1'',2'}$=6.6, $J_g$=14.4 and 4.18 dd(1H), $J_{1',2'}$=3.2, $J_g$=14.4 1'-CH$_2$; 7.87 s(1H), H-8; cyclopropyl: 2.84 m(1H) CH; 0.70 m(2H)+0.94 m(2H) CH$_2$.C$_{12}$H$_{20}$N$_6$O$_4$P (343.4) calc. C, 41.97; H, 5.87; N, 24.48; P, 9.04. found C, 41.76; H, 6.05; N, 24.77; P, 9.21.

EXAMPLE 39

9-(R)-(2-Phosphonomethoxypropyl)-2-amino-6-cyclopentylaminopurine

A mixture of di(2-propyl) 9-(R)-(2-phosphonomethoxypropyl)-2-amino-6-chloropurine (0.50 g, prepared according to Example 26), cyclopentylamine (2.0 ml) and ethanol (20 ml) is refluxed under exclusion of moisture for 12 h and evaporated in vacuo. The work-up of the reaction mixture, following reaction with bromotrimethylsilane and isolation of the product is performed essentially as described in Example 34. Yield, 0.36 g (76%) of 9-(R)-(2-phosphonomethoxypropyl)-2-amino-6-cyclopentylaminopurine, m.p. 167–170° C., $[\alpha]_D=-17.1°$ (c=0.5, 0.1M HCl). $^1$H-NMR spectrum (D$_2$O+NaOD): 1.17 d(3H), $J_{3',2'}$=6.3, CH$_3$; 3.67 dd(1H), $J_{P,CH}$=7.8, $J_g$=12.2 and 3.56 dd (1H) $J_{P,CH}$=9.3, $J_g$=12.2, P—CH$_2$; 3.97 br sext (1H), 2'-CH, ΣJ=29.1; 4.18 d(2H), $J_{1',2'}$=5.1, 1'-CH$_2$; 7.92 s(1H), H-8; cyclopentyl: 4.33 m(1H) CH; 2.00 m (2H)+1.70 m(2H) CH$_2$+1.60m (2H)+1.54 m (2H). C$_{14}$H$_{24}$N$_6$O$_4$P (371.4) calc. C, 45.27; H, 6.51; N, 22.63; P, 8.36. found C, 44.89; H, 6.45; N, 22.77; P, 8.23.

EXAMPLE 40

9-(R)-(2-Phosphonomethoxypropyl)-2-amino-6-cyclohexylaminopurine

A mixture of di(2-propyl) 9-(R)-(2-phosphonomethoxypropyl)-2-amino-6-chloropurine (0.50 g, prepared according to Example 26), cyclohexylamine (2.0 ml) and ethanol (20 ml) is refluxed under exclusion of moisture for 10 h and evaporated in vacuo. The work-up of the reaction mixture, following reaction with bromotrimethylsilane and isolation of the product is performed essentially as described in Example 34. Yield, 0.32 g (65%) of 9-(R)-(2-phosphonomethoxypropyl)-2-amino-6-cyclohexylaminopurine, m.p. 164–165° C., $[\alpha]_D=-15.9°$ (c=0.5, 0.1M HCl). $^1$H-NMR spectrum (D$_2$O+NaOD):1.12 d(3H), $J_{3',2'}$=6.3; 3.43 dd(1H), $J_{P,CH}$=9.3, $J_g$=12.4 and 3.5 d (1H) $J_{P,CH}$=9.3, $J_g$=12.4, P—CH$_2$; 3.93 m, 2'-CH; 4.10 dd(1H), $J_{1'',2'}$=5.6, $J_g$=14.6 and 4.18 dd(1H), $J_{1',2'}$=4.4, $J_g$=14.6 1'-CH$_2$; 7.92 s(1H), H-8; cyclohexyl: 3.90 m(1H) CH; 1.15–1.42 m(5H)+1.62 m(1H)+1.75 m(2H)+1.95 m(2H) CH$_2$.C$_{15}$H$_{25}$N$_6$O$_4$P (384.4) calc. C, 46.86; H, 6.56; N, 21.87; P, 8.07. found C, 46.44; H, 6.85; N, 22.07; P, 8.21.

EXAMPLE 41

9-(R)-(2-Phosphonomethoxypropyl)-2-amino-6-pyrrolidinopurine

A mixture of di(2-propyl) 9-(R)-(2-phosphonomethoxypropyl)-2-amino-6-chloropurine (0.50 g, prepared according to Example 26), pyrrolidine (2.0 ml) and ethanol (20 ml) is refluxed under exclusion of moisture for 6 h and evaporated in vacuo. The work-up of the reaction mixture, following reaction with bromotrimethylsilane and isolation of the product is performed essentially as described in Example 34. Yield, 0.35 g (78%) of 9-(R)-(2-phosphonomethoxypropyl)-2-amino-6-pyrrolidinopurine, m.p.181–182° C., $[\alpha]_D=-17.4°$ (c=0.5, 0.1M HCl). $^1$H-NMR spectrum (D$_2$O+NaOD):1.21 d(3H), $J_{3',2'}$=6.1, $CH_3$; 3.57 dd(1H), $J_{P,CH}$=9.5, $J_g$=12.2 and 3.65 dd (1H) $J_{P,CH}$=9.5, $J_g$=12.2, P—$CH_2$; 3.98 br sext(1H) 2'-CH; 4.18 d(2H), $J_{1',2'}$=4.9, 1'-$CH_2$; 7.85 s(1H), H-8; pyrrolidin-1-yl: 3.41 br(2H) and 3.75 br(2H) N—$CH_2$; 1.93br(2H)+2.00 br(2H) C—$CH_2$. $C_{13}H_{21}N_6O_4P$ (356.4) calc. C, 43.81; H, 5.94; N, 23.58; P, 8.71. found C, 43.45; H, 6.17; N, 23.87; P, 8.82.

EXAMPLE 42

9-(R)-(2-Phosphonomethoxypropyl)-2-amino-6-piperidinopurine

A mixture of di(2-propyl) 9-(R)-(2-phosphonomethoxypropyl)-2-amino-6-chloropurine (0.50 g, prepared according to Example 26), piperidine (2.0 ml) and ethanol (20 ml) is refluxed under exclusion of moisture for 3 h and evaporated in vacuo. The work-up of the reaction mixture, following reaction with bromotrimethylsilane and isolation of the product is performed essentially as described in Example 34. Yield, 0.40 g (84%) of 9-(R)-(2-phosphonomethoxypropyl)-2-amino-6-piperidinopurine, m.p.154–156° C., $[\alpha]_D$=-0.8° (c=0.5, 0.1M HCl). $^1$H-NMR spectrum ($D_2O$+NaOD):1.14 d(3H), $J_{3',2'}$=6.1, $CH_3$; 3.44 dd(1H), $J_{P,CH}$=9.0, $J_g$=12.4 and 3.55 dd (1H) $J_{P,CH}$=9.3, $J_g$=12.4, P—$CH_2$; 3.93 m(1H) 2'-CH; 4.09 d(2H) $J_{1',2'}$=6.1, $J_g$=14.4 and 4.17 dd(1H), $J_{1',2'}$=4.1, $J_g$=14.4 1'-$CH_2$; 7.88 s(1H), H-8; piperidin-1-yl: 3.95 br t(4H), J=5.4 N—$CH_2$; 1.60 m (4H)+1.69 m(2H) C—$CH_2$. $C_{14}H_{23}N_6O_4P$ (370.4) calc. C, 45.40; H, 6.26; N, 22.69; P, 8.36. found C, 45.68; H, 5.94; N, 22.46; P, 8.41.

EXAMPLE 43

9-(R)-(2-Phosphonomethoxypropyl)-2-amino-6-morpholinopurine

A mixture of di(2-propyl) 9-(R)-(2-phosphonomethoxypropyl)-2-amino-6-chloropurine (0.50 g, prepared according to Example 26), morpholine (2.0 ml) and ethanol (20 ml) is refluxed under exclusion of moisture for 2 h and evaporated in vacuo. The work-up of the reaction mixture, following reaction with bromotrimethylsilane and isolation of the product is performed essentially as described in Example 34. Yield, 0.45 g (94.5%) of 9-(R)-(2-phosphonomethoxypropyl)-2-amino-6-morpholinopurine, m.p.160–162° C., $[\alpha]_D$=+7.1° (c=0.5, 0.1M HCl). $^1$H-NMR spectrum ($D_2O$+NaOD):1.15 d(3H), $J_{3',2'}$=6.1; 3.50 dd(1H), $J_{P,CH}$=9.8, $J_g$=12.9 and 3.68 dd (1H) $J_{P,CH}$=9.3, $J_g$=12.9, P—$CH_2$; 3.90 m(1H) 2'-CH; 4.05 d(2H) $J_{1',2'}$=6.6, $J_g$=14.4 and 4.18 dd(1H), $J_{1',2'}$=3.2, $J_g$=14.4 1'-$CH_2$; 7.81 s(1H), H-8; morpholin-1-yl: 4.03 br t(4H), J=4.5 N—$CH_2$; 3.80 br t(4H) C—$CH_2$.$C_{13}H_{21}N_6O_5P$ (372.3) calc. C, 41.94; H, 5.69; N, 22.57; P, 8.32. found C, 42.03; H, 5.66; N, 22.16; P, 8.62.

EXAMPLE 44

9-(R)-(2-Phosphonomethoxypropyl)-2-amino-6-benzylaminopurine

A mixture of di(2-propyl) 9-(R)-(2-phosphonomethoxypropyl)-2-amino-6-chloropurine (0.50 g, prepared according to Example 26), benzylamine (2.0 ml) and ethanol (20 ml) is refluxed under exclusion of moisture for 6 h and evaporated in vacuo. The work-up of the reaction mixture, following reaction with bromotrimethylsilane and isolation of the product is performed essentially as described in Example 34. Yield, 0.45 g (90%) of 9-(R)-(2-phosphonomethoxypropyl)-2-amino-6-benzylaminopurine, m.p.158–160° C., $[\alpha]_D$=-4.9° (c=0.5, 0.1M HCl). $^1$H-NMR spectrum ($D_2O$+NaOD):1.13 d(3H), $J_{3',2'}$=5.9; 3.52 dd(1H), $J_{P,CH}$=10.3, $J_g$=12.0 and 3.68 dd (1H) $J_{P,CH}$=10.0, $J_g$=12.0, P—$CH_2$; 3.86 m(1H) 2'-CH; 3.99 d(2H) $J_{1'',2'}$=5.6, $J_g$=14.4 and 4.09 dd(1H), $J_{1',2'}$=3.5, $J_g$=14.4 1'-$CH_2$; 7.77 s(1H), H-8; arom.protons: 7.22 m(5H); 4.58 br s(2H) benzyl-$CH_2$. $C_{16}H_{21}N_6O_4P$ (392.3) calc. C, 48.98; H, 5.39; N, 21.42; P, 7.89. found C, 49.16; H, 5.37; N, 21.23; P, 7.86.

EXAMPLE 45

9-(S)-(2-Phosphonomethoxypropyl)-8-azaguanine and 8-(S)-(2-Phosphonomethoxypropyl)-8-azaguanine A mixture of 8-azaguanine (3.5 g), dimethylformamide (35 ml) and dimethylformamide dineopentyl acetal (15 ml) is heated at 80° C. 16 h under exclusion of moisture. After cooling at room temperature, the precipitated product is filtered by suction, washed with ethanol and ether and dried in vacuo. Yield, 3.1 g (65%) N2-dimethylaminomethylene-8-azaguanine, HPLC pure.

The mixture of this compound (2.1 g, 10 mmol), cesium carbonate (1.75 g, 5.4 mmol) and (S)-2-[(di(2-propyl) phosphonylmethoxy]-1-toluenesulfonyloxypropane in dimethylformamide (40 ml) is stirred for 4 h at 100° C. under exclusion of moisture. The mixture is filtered while hot, evaporated at 40° C./13 Pa and the residue treated with a mixture of methanol and conc.aqueous ammonia (1:1, 200 ml) overnight at ambient temperature. The solvents are evaporated in vacuo and the residue chromatographed on a column of silica gel (200 ml) in methanol-chloroform mixture (5:95). The fluorescent product (Rf=0.42, TLC in methanol-chloroform, 1:9, silica gel plate), amorphous foam, yield 0.9 g (23%) is dried in vacuo and treated with acetonitrile (25 ml) and bromotrimethylsilane (2.5 ml) overnight at room temperature. The work-up of the mixture is performed as described in Example 34. The product is isolated by ion exchange chromatography on Dowex 50×8 ($H^+$-form) and crystallized from water. Yield, 0.45 g.

Further elution of the silica gel column affords the 9-isomer (Rf=0.36, TLC in methanol-chloroform, 1:9, silica gel plate) in the yield of 0.9 g (23%). Conversion by bromotrimethylsilane in acetonitrile (Example 34) gives after deionization and crystallization from water 9-(S)-(2-phosphonomethoxypropyl)-8-azaguanine (0.50 g, HPLC pure).

EXAMPLE 46

9-(R)-(2-Phosphonomethoxypropyl)-8-azaquanine, 8-(R)-(2-Phosphonomethoxypropyl)-8-azaquanine and 7-(R)-(2-Phosphonomethoxypropyl)-8-azaquanine The reaction is performed essentially as described for the (S)-enantiomers in Example 44. After the work-up of the condensation mixture with aqueous methanolic ammonia the crude mixture of bis(2-propyl)esters is applied onto a column of Dowex 50×8 (H+-form) (150 ml) and the column eluted with 20% aqueous methanol. The UV-absorbing fraction is taken down in vacuo and dried affording the 9-isomer as an amorphous foam. The residue is treated with acetonitrile (30 ml) and bromotrimethylsilane (3 ml) overnight, evaporated in vacuo, the residue dissolved in 2.5% ammonia and reevaporated in vacuo. This residue is applied onto a column (100 ml) Dowex 1×2 (acetate form) and washed with water (1 l) and with 1 M acetic acid (500 ml). The eluates are discarded and the resin extracted on filter with boiling water (500 ml). This eluate is evaporated in vacuo and the residue crystallized from water (poorly soluble) to afford the 9-(R)-isomer (0.50 g). For $C_8H_{13}N_6O_5P$ (304.2) calculated: 31.59%; C, 4.31%; H, 27.62%;N, 10.18%;P. found 32.10%;C, 4.35%; H, 27.44%; N, 10.30%; P.

Further elution of Dowex 50 column with 2.5% aqueous ammonia gives an UV-absorbing fraction which is evaporated in vacuo, dried and treated with acetonitrile (20 ml) and bromotrimethylsilane (2 ml). The reaction mixture is evaporated and the residue dissolved by the addition of 5% aqueous ammonia (100 ml), and the mixture is deionized on a column (100 ml) Dowex 50×8 (H$^+$-form). The ammonia eluate affords gel forming mixture which is dissolved in water by addition of ammonia and applied onto a column of Sephadex A-25 (150 ml) in 0.02 M triethylammonium hydrogen carbonate. The column is eluted with a linear gradient of the same buffer (0.02–0.20 M, 1 l each) to give the main fraction consisting of the mixture of the 7- and 8-isomer ($E_{Up}$ 0.92, fluorescent spot). The residue after codistillation with methanol is applied onto a column (20 ml) Dowex 1×2 (acetate), the column washed with water (100 ml) and the product eluted with 1 M acetic acid. After evaporation in vacuo, codistillation with water and trituration with ethanol the product is filtered, washed with ethanol and ether, and dried to afford 0.50 g of the mixture of 7-isomer and 8-isomer in the ratio 1:4 (by $^{13}$C-NMR). The 7- and 8-regioisomers were separated by chromatography on DEAE Sephadex A25, using elution by a 0.02 to 0.2 molar gradient of aqueous triethylammonium hydrocarbonate at pH 7.5. For $C_8H_{13}N_6O_5P$ (304.2) calculated: 31.59%; C, 4.31%; H, 27.62%;N, 10.18%;P. found 32.10%;C, 4.35%; H, 27.44%; N, 10.30%; P. $^1$H-NMR (D$_2$O+NaOD): 8-Isomer: 4.65 2×dd, 2H ($J_{1'2'}$=5.4,$J_{1"2'}$=5.1,$J_g$=14.0) 1'-CH$_2$; 4.17 br sext, 1H (J=29.5) 2'-CH; 3.52 dd, 1H ($J_{PCH}$=9.7, $J_g$=12.2)+3.47 dd, 1H ($J_{PCH}$=9.0, $J_g$=12.2) P—CH$_2$; 1.18 d, 3H ($J_{3'2'}$=6.3); 7-Isomer 4.76 2×dd, 2H ($J_{1'2'}$, $J_{1"2'}$=5.2, $J_g$=14.0) 1'-CH$_2$; 4.13 br sext, 1H (J=29.5) 2'-CH; 3.50 m, P—CH$_2$; 1.16 d, 3H ($J_{3'2'}$=6.3).

EXAMPLE 47

9-(R)-(2-Phosphonomethoxypropyl)-8-aza-2,6-diaminopurine and 8-(R)-(2-Phosphonomethoxypropyl)-8-aza-2,6-diaminopurine A suspension of 8-aza-2,6-diaminopurine hemisulfate (25 mmol) in water (100 ml) is stirred under addition of Dowex 50×8 (H$^+$-form) until dissolution, the suspension was poured onto a column of the same cation exchanger (100 ml) and the column is washed with water until neutral. The resin is then suspended in water (200 ml) and treated with aqueous ammonia until alkaline, filtered and washed with boiling water (total, 1 l). The filtrate and washings are taken to dryness in vacuo, the residue codistilled with ethanol (2×50 ml) and the obtained free 8-aza-2,6-diaminopurine filtered from ether, washed with the same solvent and dried over phosphorus pentoxide in vacuo.

A suspension of this compound (3.02 g, 20 mmol) and cesium carbonate (3.3 g, 10 mmol) in dimethylformamide (60 ml) is heated at 100° C. for 1 h and a solution of (R)-2-[(di(2-propyl)phosphonylmethoxy]-1-toluenesulfonyloxypropane (8.6 g, 21 mmol) in dimethylformamide (30 ml) is added over 15 min under stirring. The heating and stirring is then continued for additional 16 h, the mixture stripped of the solvent in vacuo and the residue extracted with boiling chloroform (total, 300 ml). The extract is chromatographed on a column (250 ml) silica gel in chloroform and the column eluted with chloroform-methanol mixture (95:5). The elution affords di(2-propyl) 9-(R)-(2-phosphonomethoxypropyl)-8-aza-2,6-diaminopurine ($R_F$0.70, TLC on silica gel, chloroform-methanol, 4:1) which after evaporation of the relevant fractions and crystallization from ethyl acetate-petroleum ether gives 1.75 g (22.5%) of a crystalline material, m.p.120–122° C., $[\alpha]_D$=4.7° (c=0.5, 0.1M HCl). For $C_{14}H_{26}N_7O_4P$ (387.5) calculated: C, 43.40; H, 6.76; N, 25.31; P, 8.01. found C, 43.07; H, 6.80; N, 25.21; and 8.02%; P. NMR-Spectrum:1.10+1.12+1.14+1.16+1.17, 5×d (3H each), J=6.1), CH$_3$; 4.11 pent d (ΣJ=29.5) 2'-CH; 4.28 2×dd, 1H ($J_{1"2'}$=4.90, $J_g$=14.4) 1'-CH$_2$; 4.34 dd,1H ($J_{1'2'}$=7.1, $J_g$=14.4) 2'-CH; 3.65 dd, 1H ($J_{PCH}$=9.0, $J_g$=12.7)+3.74 dd, 1H ($J_{PCH}$=9.5, $J_g$=12.27) P—CH$_2$; 4.43 dq (1H) (J=6.1)+ 4.47 (J=6.3, $J_P$—O—CH=7.8) P—OCH; 7.35+7.70, 2×br (2×1H) NH$_2$; 6.37 brs (2H) NH$_2$.

This product is treated with acetonitrile (25 ml) and bromotrimethylsilane (2.5 ml) overnight at room temperature and the solution evaporated in vacuo. Water (50 ml) is added, the mixture alkalized by addition of conc. aqueous ammonia and the solution evaporated. Further work-up and purification is performed essentially as described in Example 17. Yield, 0.90 g (65.5%) 9-(R)-(2-phosphonomethoxypropyl)-2,6-diamino-8-azaadenine, m.p. 238–242° C., $[\alpha]_D$=+5.6° (c=0.5, 0.1M HCl). $^1$H-NMR spectrum (D$_2$O+NaOD): 1.17 d(3H),($J_{3',2'}$=6.3) CH$_3$; 3.50 dd(1H), $J_{P,CH}$=9.1, $J_g$=12.2 and 3.59 dd(1H) $J_{P,CH}$=9.3, $J_g$=12.2, P—CH$_2$; 4.08 m, ΣJ=30.0 2'-CH; 4.45 dd(1H), $J_{1"2'}$=5.4, $J_g$=14.9 and 4.49 dd(1H), $J_{1'2'}$=5.6, $J_g$=14.9 1'-CH$_2$. For $C_8H_{14}N_7O_4P$ (305.3) calc. C, 31.47; H, 4.62; N, 32,12; P, 10.17. found C, 31.71; H, 5.02; N, 31.88; P, 9.96. $E_{Up}$(pH7.5)=0.85.

Further elution of the silica gel column gives 1.40 g (18%) of di(2-propyl) 8-(R)-(2-phosphonomethoxypropyl)-8-aza-2,6-diaminopurine ($R_F$0.50, TLC on silica gel, chloroform-methanol, 4:1), m.p.148–150° C. (ethyl acetate-petroleum ether), $[\alpha]_D$=−43.7° (c=0.5, 0.1M HCl). For $C_{14}H_{26}N_7O_4P$ (387.5) calculated: C, 43.40; H, 6.76; N, 25.31; P, 8.01. found C, 43.15; H, 6.75; N, 25.16; and 7.96%; P. NMR-Spectrum:1.10+1.11+1.14+1.16+1.18, 5×d (3H each), J=6.1) CH$_3$; 4.17 pent d (ΣJ=31.0) 2'-CH; 4.50 dd, 1H ($J_{1'2'}$=6.60, $J_g$=13.9)+4.53 dd, 1H ($J_{1'2'}$=5.4, $J_g$=13.9) 1'-CH$_2$; 4.47+4.43 2×dq, 2H ($J_{P—OCH}$=7.6, JCH,CH$_3$=6.1) P—OCH; 3.63 dd, 1H ($J_{PCH}$=9.0, $J_g$=12.7)+3.75 dd, 1H ($J_{PCH}$=9.5, $J_g$=12.7) P—CH$_2$; 7.50+6.08, 2×br (2×2H) NH$_2$. The reaction with bromotrimethylsilane is performed essentially as described for the 9-isomer; yield, 0.80 g (72.5%) 8-(R)-(2-phosphonomethoxypropyl)-8-aza-2,6-diaminopurine, m.p. 238–240° C., $[\alpha]_D$=−23.5° (c=0.5, 0.1M HCl). $^1$H-NMR spectrum (D$_2$O+NaOD): 1.21 d(3H), ($J_{3',2'}$=6.3) CH$_3$; 3.50 dd(1H), $J_{P,CH}$=9.2, $J_g$=12.2 and 3.58 dd(1H) ($J_{P,CH}$=9.4, $J_g$=12.2) P—CH$_2$; 4.17 m, ΣJ=29.3 2'-CH; 4.70 d(2H), $J_{1'2'}$=5.2) 1'-CH$_2$. For $C_8H_{14}N_7O_4P$ (305.3) calc. C, 31.47; H, 4.62; N, 32.12; P, 10.17. found C, 30.74; H, 4.55; N, 29.90; P, 10.16. $E_{Up}$(pH7.5)=0.85.

EXAMPLE 48

9-(R)-(2-Phosphonomethoxypropyl)-6-mercaptopurine

Sodium hydride (0.40 g, 60% dispersion in paraffin, 10 mmol) is added to a solution of 6-chloropurine (1.55 g, 10 mmol) in dimethylformamide (25 ml) and the mixture stirred for 1 h at ambient temperature. A solution of (R)-2-[(di(2-propyl)phosphonylmethoxy]-1- toluenesulfonyloxypropane (6.5 g, 15.9 mmol) in dimethylformamide (50 ml) is added and the mixture stirred at 60° C. for 8 h. The mixture is then stripped off the solvent in vacuo and the residue extracted with hot chloroform (total, 250 ml). The extract is then evaporated in vacuo and the residue chromatographed on a column (250 ml) of silica gel in chloroform. The product is eluted with chlorofom-methanol (95:5) and the relevant fractions containing product were evaporated to dryness. Yield, 2.35 g (60%) of the oily di(2-propyl) 8-(R)-(2-phosphonomethoxypropyl)-6-chloropurine ($R_F$ 0.70, TLC on silica gel, chloroform-methanol, 4:1), m.p.148–150° C. (ethyl acetate-petroleum ether), $[\alpha]_D=-43.7°$ (c=0.5, 0.1M HCl). For $C_{15}H_{24}ClN_4O_4P$ (390.9): Mass spectrum:391($M^+$), 348 (M-ipr), 306 (M-2×iPr); NMR-Spectrum: 1.05 d (3H), J=6.1) $CH_3$; 4.02 pent d ($\Sigma J$=28.9) 2'-CH; 4.30 dd, 1H ($J_{1'',2'}$=7.00, $J_g$=14.3)+4.45 dd, 1H ($J_{1',2'}$=3.6, $J_g$=14.3) 1'-$CH_2$; 4.49 m, 2H ($J_{P\text{—}OCH}$=7.6) P—OCH; 3.68 dd, 1H ($J_{PCH}$=9.8, $J_g$=13.7)+3.82 dd, 1H($J_{PCH}$=9.2, $J_g$=13.7) P—$CH_2$; 1.12+1.13 (3×d, 4×3H), J=6.1, J=6.3) $CH_3$ (2-propyl); 8.61+8.77, 2×s, 2H, H-2+H-8.

This product is treated with thiourea (2 g) in ethanol at reflux for 1 h, the solution is alkalized with triethylamine, taken down. to dryness and the residue extracted with chloroform (200 ml). The extract is evaporated in vacuo and the residue ($R_F$ 0.63, TLC on silica gel, chloroform-methanol, 4:1) dried in vacuo. Acetonitrile (40 ml) and bromotrimethylsilane (4 ml) is added and the mixture stirred till dissolution. The mixture is left to stand overnight at room temperature, taken down to dryness in vacuo and dissolved in water (100 ml) by alkalization with conc.aqueous ammonia. The alkaline solution is then evaporated in vacuo and the residue in water (20 ml) (alkalized by ammonia) is applied onto a column (150 ml) Sephadex A-25 equilibrated with 0.05 M triethylammonium hydrogen carbonate (pH 7.5). The column is eluted with the same buffer until the absorption of the eluate drops to the original value and then with linear gradient (0.02M–0.2M triethylammonium hydrogen carbonate (pH 7.5) (1l each). The main UV absorbing fraction is taken down to dryness and codistilled with methanol (5×50 ml) in vacuo. The residue is applied in 10 ml water on a column (50 ml) Dowex 1×2 (acetate form), the column washed with water and the ionex stirred in 10% aqueous formic acid (200 ml) for 15 min. The suspension is filtered and the resin washed repeatedly with boiling water (total, 1 l). The filtrates gaffords on concentration in vacuo and recrystallization from water 9-(R)-(2-phosphonomethoxypropyl)-6-thiopurine (0.90 g, 49%), m.p.156–158° C., $[\alpha]_D=-1.7°$ (c=0.5, 0.1HCl). $^1$H-NMR-Spectrum ($D_2O$+NaOD): 1.25 d(3H),($J_{3',2'}$=5.4) $CH_3$; 3.57 dd(1H), $J_{P,CH}$=9.5, $J_g$=12.2 and 3.79 dd(1H) ($J_{P,CH}$=9.5, $J_g$=12.2) P—$CH_2$; 4.02 m 2'-CH; 4.31 d(2H) ($J_{1'',2'}$=6.8)+ 4.52 d, 2H ($J_{1',2'}$<2.0, $J_g$=14.4) 1'-$CH_2$; 8.35+8.72, 2×s (2H) H-2+H-8. For $C_9H_{13}N_4O_4PS$ (304.0) calc. C, 35.52; H, 4.31; N, 18.42; P, 10.19; S, 10.50. found C, 35.34; H, 4.70; N, 18.26; P, 10.76.

EXAMPLE 49

9-(R)-(2-Phosphonomethoxypropyl)-N1,N6-ethenoadenine

A solution of 9-(R)-(2-phosphonomethoxypropyl)adenine (0.40 g) in 1M chloroacetaldehyde solution in water (20 ml) is incubated at 37° C. for 48 h and evaporated in vacuo. The residue in water (10 ml) is applied on a column (250 ml) octadecylsilica gel (20–30 µ) and washed with water (3 ml/min). The fractions (20 ml) are analyzed by HPLC in 0.05 M triethylammonium hydrogen carbonate pH 7.5 and the appropriate fractions pooled and taken down in vacuo. The product is triturated with ethanol and filtered. Yield, 0.35 g (80%), m.p.180–182° C., $[\alpha]_D=-25.6°$ (c=0.5, 0.1M HCl). For $C_{11}H_{14}N_5O_4P$ (311.3) calc. C, 42.44; H, 4.53; N, 22.50; P, 9.97. found C, 42.30; H, 4.75; N, 22.24; P, 10.25.

EXAMPLE 50

Evaluation Against Human Immunodeficiency Virus (HIV) and Moloney Murine Sarcoma Virus (MSV) in Vitro The activity of the compounds against HIV-1 and HIV-2 induced cytopathicity was examined in human lymphocyte MT-4 cells. The cells (250 000 cells/ml) were infected with 100 $CCID_{50}$ (1 CCID is a virus quantity which causes cytopathicity effect in 50% of the cells under the experimental conditions) of HIV-1 or HIV-2 and added to 200 µl-wells of a microtiter plate containing different dilutions of the test compounds. The infected cell cultures were then incubated at 37° C. for 5 days in a humidified $CO_2$-controlled incubator. Then, the cytopathicity of the virus was examined by determination of MT-4 cell viability by trypan blue dye staining. The results are summarized in Table 1 in comparison with the data on the prototype compounds.

Also shown in Table 1 are results of testing the activity of the compounds against MSV-induced transformation in murine embryo fibroblast C3H/3T3 cells. The cells were seeded in 1-ml-wells of a 48-well microtiter plate and exposed to 80 PFU (plaque forming units) for 60–90 minutes. Then, the virus was removed and culture medium containing appropriate concentrations of the test compounds were added (1 ml per well). At day 6 post infection, MSV-induced transformation of the cell culture was examined microscopically. The results are summarized in Table 1 in comparison with the data on the prototype compounds.

TABLE 1

Anti-retrovirus activity of the (S)- and (R)-enantiomers of the compounds of Formula I in comparison with other acyclic nucleoside phosphonates.

| | MT-4 | | C3H/3T3 | | |
|---|---|---|---|---|---|
| | EC50[a] (µg/ml) | | CC50[b] (µg/ml) | EC50[c] (µg/ml) | MIC[d] (µg/ml) |
| Compound | HIV-1 | HIV-2 | MSV | | |
| (S)-PMPA | 78 | 63 | >100 | 120 | >100 |
| (R)-PMPA | 1.7 | 1.4 | >100 | 0.99 | >100 |
| (S)-PMPDAP | 2.0 | 4.0 | >100 | 2.9 | >100 |
| (R)-PMPDAP | 0.05 | 0.06 | >100 | 0.14 | >100 |
| (S)-PMPG | 1.2 | 1.3 | 45 | 0.95 | 8 |
| (R)-PMPG | 1.8 | 1.7 | >100 | 0.15 | 40 |
| (R)-9-PMP-8-azaA | 2.42 ± 0.91 | 1.75 ± 0.2 | | 0.43 ± 0.24 | |
| (R)-9-PMP-6-thioPu | >100 | >100 | | 18 ± 10 | |
| (R)-7/8PMP-8-azaG* | >0.16 | >0.16 | | 1.1 ± 0.6 | |
| (R)-9-PMP-6-piperidino-DAP | >100 | >100 | | 12.6 ± 10 | |
| (R)-9-PMP-6-morpholino-DAP | >100 | >100 | | 6.1 ± 2.3 | |
| (R)-9-PMP-6-cyclohexyl-DAP | 8.0 ± 2 | 7 ± 2.6 | | 1.4 ± 1.2 | |
| (R)-9-PMP-6-benzyl-DAP | 10.3 ± 1.4 | 8 ± 2.9 | | 0.3 ± 0.11 | |
| (R)-9-PMP-6-dimethyl-DAP | 2.3 ± 0.2 | 4.2 ± 2.8 | | 3.25 ± 1.44 | |

TABLE 1-continued

Anti-retrovirus activity of the (S)- and (R)-enantiomers of the compounds of Formula I in comparison with other acyclic nucleoside phosphonates.

| | MT-4 | | C3H/3T3 | |
|---|---|---|---|---|
| | EC50[a] (μg/ml) | CC50[b] (μg/ml) | EC50[c] (μg/ml) | MIC[d] (μg/ml) |
| Compound | HIV-1 | HIV-2 | MSV | |
| (R)-9-PMP-6-butyl-DAP | 13.1 ± 4.3 | 9.8 ± 4.9 | | 3.27 ± 1.3 |
| (R)-9-PMP-6-(2-butyl)-DAP | 30 ± 19 | 25 ± 15 | | 3.5 ± 0.3 |
| (R)-9-PMP-6-thioG | >100 | >100 | | 3.94 ± 2.13 |
| PMEA | 2 | 2 | 67 | 2 | >100 |
| (S)-FPMPA | 2.7 | 2.6 | >100 | 1.5 | >100 |
| (R)-FPHPA | 83 | 54 | >100 | >100 | >100 |
| (S)-FPMPDAP | 4.8 | 3.3 | >100 | 1.7 | >100 |
| (R)-FPMPDAP | 1.4 | 1.5 | >100 | 1.7 | >100 |

[a]Compound concentration required to inhibit HIV-induced cytopathicity in MT-4 cells by 50%;
[b]Compound concentration required to reduce MT-4 cell viability by 50%;
[c]Compound concentration required to inhibit MSV-induced C3H/3T3 cell transformation by 50%;
[d]Compound concentration that results in a microscopic alteration of the cell culture morphology.
Abbreviations
FPMP N-(3-fluoro-2-phosphonomethoxypropyl)derivative of the Formula 4;
PME N-(2-phosphonomethoxyethyl) derivative of the Formula 3;
PMP N-(2-phosphonomethoxypropyl) derivative of the Formula I;
A adenine, DAP 2,6-diaminopurine, G guanine.
*Regioisomeric mixture

Conclusions (1) Most of the resolved compounds of the Formula I examined showed marked anti-HIV activity in vitro. HIV-1 and HIV-2 did not differ in their sensitivity to the test compounds.

(2) (R)-PMPA was markedly inhibitory to retrovirus replication at 1–2 μg/ml and non-toxic to the cells at 100 mg/ml. Its selectivity index (ratio cytotoxic dose/antivirally active dose) proved superior over that of the prototype compound PMEA. The (S)-enantiomer of PMEA was devoid of marked antiretroviral activity.

(3) (R)-PMPDAP was exquisitely inhibitory to retrovirus replication (EC$_{50}$ 0.01–0.1 μg/ml) and non-toxic to the cells at 100 μg/ml. It proved superior over PMEA and other prototype compounds in terms of both antiviral activity and lack of toxicity. Its selectivity index was >2 000 for HIV-1 and HIV-2.

EXAMPLE 51

Treatment of Moloney Murine Sarcoma Virus (MSV) Infection in Mice by Intraperitoneal Administration Two gram newborn NMRI mice were injected intramuscularly in the left hind leg with 50 μl of 250-fold diluted stock preparation of Moloney murine sarcoma virus. Starting 2–4 hours before virus infection, each animal was injected intraperitoneally in groups of 10 with a single dose of test compound with 50, 20 or 10 mg/kg of the resolved compounds of the Formula I or prototype compounds (for abbreviations, see Footnote to Table 1); compounds (R)-PMPA and (R)-PMPDAP were administered also at the dose of 5 and 2 mg/kg. Another group of mice (20 animals) was administered RPMI-1640 medium as placebo. All compounds were solubilized in RPMI-1640 medium. The mice were observed daily for 20 days and the day of tumor initiation and the day of animal death was recorded for each animal. Statistical analyses were performed by calculating the standard deviation. The summarized results are shown in the Table 2.

TABLE 2

Inhibitory effect of (S)- and (R)-enantiomers of the compounds of the Formula I and prototype acyclic nucleoside phosphonates administered by intraperitoneal route on MSV-induced tumor formation and associated death in NMRI mice.

| Compound | Dose (mg/kg) | Number of mice | Mean day of tumor initiation[a] | Mean day of animal death[b] |
|---|---|---|---|---|
| (S)-PMPA | 50 | 20 | 5.8 ± 0.63 | 12.4 ± 0.84 |
| | 20 | 20 | 4.5 ± 0.71 | 10.9 ± 0.88 |
| | 10 | 20 | 4.7 ± 0.95 | 10.9 ± 0.88 |
| (R)-PMPA | 50 | 10 | >20 (100%) | >20 (100%) |
| | 20 | 10 | 13.5 ± 3.5 (80%) | >20 (100%) |
| | 10 | 20 | 12.9 ± 2.2 (75%) | 18.3 ± 1.10 (85%) |
| | 5 | 10 | 7.11 ± 1.5 (10%) | 14.4 ± 0.47 (20%) |
| | 2 | 10 | 5.3 ± 1.1 | 12.6 ± 1.26 |
| (R)-PMPDAP | 20 | 19 | 11 (95) | 18 (95) |
| | 10 | 20 | 11.5 (90) | 18.5 (90) |
| | 5 | 20 | 12.8 (70) | 16.5 (90) |
| | 2 | 20 | 11 (36) | 15 (70) |
| PMEA | 50 | 10 | 9.0 (90%) | 16.0 (90%) |
| | 20 | 30 | 10.6 ± 2.0 (44%) | 14.7 ± 1.8 (66%) |
| | 10 | 20 | 9.8 ± 1.9 (24%) | 14.2 ± 2.5 (43%) |
| (S)-FPMPA | 50 | 10 | >20 (100 %) | >20 (100%) |
| | 20 | 20 | 11 ± 2.7 (31%) | 17.2 ± 2.2 (55%) |
| | 10 | 20 | 7.7 ± 2.4 | 13.6 ± 2.8 (40%) |
| (R)-FPMPA | 50 | 10 | 4.7 ± 0.67 | 11.2 ± 0.92 |
| | 20 | 10 | 4.3 ± 0.48 | 10.4 ± 0.52 |
| (S)-FPMPDAP | 50 | 10 | 11.0 ± 2.1 (17%) | 16.5 ± 0.71 (67%) |
| | 25 | 10 | 8.3 ± 1.8 | 14.6 ± 2.2 |
| | 10 | 6 | 8.5 ± 2.6 | 16.7 ± 3.2 (33%) |
| (R)-FPMPDAP | 50 | 20 | 7.75 ± 1.3 | 13.9 ± 1.4 (10%) |
| | 25 | 20 | 7.7 ± 1.9 | 14.1 ± 1.5 (15%) |
| | 10 | 20 | 5.6 ± 1.0 | 12.0 ± 1.0 |
| Control | 0 | 40 | 4.65 ± 0.81 | 10.7 ± 1.2 |

[a]Values in parentheses represent percentages of MSV-infected mice without tumor at day 20 post infection.
[b]Values in parentheses represent percentages of MSV-infected mice that were still alive at day 20 post infection.

While (S)-enantiomer of PMPA (and FPMPA) has no marked antiretroviral activity in vivo at the dose of 50 mg/kg, (R)-PMPA, (R)-PMPDAP proved highly effective in inhibiting tumor initiation and prolonging the life-span of MSV-infected mice. A single (R)-PMPA dose of 50 mg/kg afforded full protection against MSV-induced tumor development. At lower doses, this compound proved superior over (S)-FPMPA in postponing the day of tumor initiation and the mean day of animal death. A single (R)-PMPDAP dose of 10–20 mg/kg gave virtually full protection of the animals (90–95%) against MSV-induced tumor development; at a dose of 2 mg/kg, significant prevention of tumor formation (in 36% of the animals) and 70% long time-survivors were observed.

Conclusion (1) (R)-PMPA proved markedly effective in increasing the mean day of tumor initiation and animal death at the single dose of 10–50 mg/kg. It is superior in these assays over the prototype compound PMEA.

(2) (R)-PMPDAP was one of the most active anti-Msv compound of the series examined in vivo. It proved five-fold superior over (R)-PMPA. It contrasts to the FPMP-series where the adenine derivative is more active in the assays than the diaminopurine counterpart.

(3) The in vivo activity of the compounds of the Formula I are in agreement with their antiviral activities against HIV and MSV in vitro.

EXAMPLE 52

Treatment of Moloney Murine Sarcoma Virus (MSV) Infection in Mice by Oral Administration Three-week-old NMRI mice (about 10 grams body weight) were injected intramuscularly in the left hind leg with 50 μl of 20-fold diluted stock preparation of Moloney murine sarcoma virus. Starting 2–4 hours before virus infection, six animals received an orally administered test compound twice a day at 100 mg/kg(total dose) daily for five subsequent days. The control (placebo) group consisted of 14 animals. The experiment was evaluated as described in Example 35. The summarized results are given in Table 3.

TABLE 3

| Compound | Number of mice | Mean day of tumor initiation | Number of mice developing tumor (%) |
| --- | --- | --- | --- |
| (R)-PMPDAP | 6 | 7.5 ± 1.0*) | 67 |
| Placebo (control) | 14 | 5.0 ± 0.0 | 100 |

*)p < 0.005 (two-sided Student's t-test).

At the dose of 100 mg/kg/day, (R)-PMPDAP increased the mean day of tumor initiation by 50%; only 67% of the mice developed a tumor.

What is claimed is:

1. A compound of the formula:

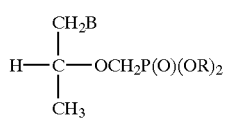
(IA)

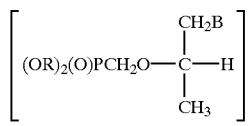
(IB)

including salts of such compounds, wherein said compound of Formula IA is substantially free of its enantiomer and wherein B is (a) an unsubstituted purine moiety, (b) a substituted purine moiety substituted independently at the 2 and/or 6 and/or 8 position by amino, halogen, hydroxy, alkoxy, alkylamino, dialkylamino, aralkylamino, pyrrolidino, morpholino, piperidino, benzoylamino, azido, mercapto or alkylthio, or (c) the 8-aza analog thereof, and wherein B is other than guanine or 2-amino-6-halopurine;

R is H; and aryl in aralkylamino is a 6–10C aromatic group.

2. The compound of claim 1 of formula IA wherein B is adenine, 2,6-diaminopurine, 2-aminopurine, 8-bromoadenine, 6-mercaptopurine, 6-thioguanine, 2-methylthioadenine, 8-azaadenine, 8-azaguanine, or 8-aza-2,6-diaminopurine.

3. The compound of claim 2 wherein B is adenine, 8-azaguanine or 2,6-diaminopurine.

4. A compound of claim 3 wherein B is 2,6-diaminopurine.

5. A method to prepare a compound of the formula:

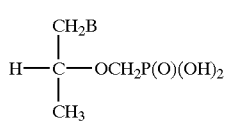
(IA)

substantially free of its enantiomer wherein B is as defined in claim 1, which method comprises hydrolyzing a compound of the formula

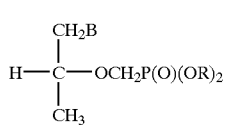
(VIIA)

which is substantially free of its enantiomer to remove R groups wherein R is independently alkyl(1–6C), aryl or aralkyl by treating with a halotrialkylsilane in a polar aprotic solvent medium.

6. The method of claim 5 wherein both R are 2-propyl.

7. The method of claim 5 wherein the compound of Formula VIIA is prepared by a process which comprises deprotecting a compound of the formula:

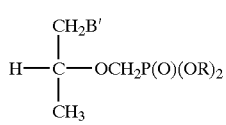
(VIA)

substantially free of its enantiomer wherein B' is a protected form of B as defined herein by treating said compound of Formula VIA with at least one deprotecting reagent.

8. The method of claim 7 wherein said compound of Formula VIA is prepared by a process which comprises reacting a compound of the formula:

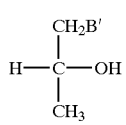
(VA)

substantially free of its enantiomer wherein B' is a protected form of B as herein defined with a compound of the formula

(IV)

wherein LvO is a leaving group, and each R independently is alkyl(1–6C), under conditions wherein said compounds of Formulas VA and IV react to form a compound of Formula VIA.

9. The method of claim 8 wherein LvO is a p-toluenesulfonyloxy (TsO) group.

10. The method of claim 5 wherein the compound of Formula VIIA is prepared by alkylating purine or pyrimidine moiety B as defined in claim 1 in the presence of alkali metal hydride or carbonate with an (R)- or (S)-2-O-dialkylphosphonylmethyl compound of the formula:

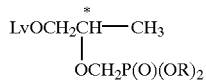 (XVII)

substantially free of its enantiomer wherein LvO is a leaving group and R is independently alkyl(1–6C), aryl or aralkyl.

11. The method of claim 10 where said alkali carbonate is cesium carbonate.

12. The method of claim 10 wherein LvO is a p-toluenesulfonyloxy (TsO) group.

13. 9-(R)-(2-Phosphonomethoxypropyl)-2-amino-6-dimethylaminopurine.

14. 9-(R)-(2-Phosphonomethoxypropyl)-2-amino-6-diethylaminopurine.

15. 9-(R)-(2-Phosphonomethoxypropyl)-2-amino-6-butylaminopurine.

16. 9-(R)-(2-Phosphonomethoxypropyl)-2-amino-6-(2-butyl)aminopurine.

17. 9-(R)-(2-Phosphonomethoxypropyl)-2-amino-6-cyclopropylaminopurine.

18. 9-(R)-(2-Phosphonomethoxypropyl)-2-amino-6-cyclopentylaminopurine.

19. 9-(R)-(2-Phosphonomethoxypropyl)-2-amino-6-cyclohexylaminopurine.

20. 9-(R)-(2-Phosphonomethoxypropyl)-2-amino-6-pyrrolidinopurine.

21. 9-(R)-(2-Phosphonomethoxypropyl)-2-amino-6-piperidinopurine.

22. 9-(R)-(2-Phosphonomethoxypropyl)-2-amino-6-morpholinopurine.

23. 9-(R)-(2-Phosphonomethoxypropyl)-2-amino-6-benzylaminopurine.

24. 9-(R)-(2-Phosphonomethoxypropyl)-8-azaguanine.

25. 8-(R)-(2-Phosphonomethoxypropyl)-8-azaguanine.

26. 7-(R)-(2-Phosphonomethoxypropyl)-8-azaguanine.

27. 9-(R)-(2-Phosphonomethoxypropyl)-8-aza-2,6-diaminopurine.

28. 8-(R)-(2-Phosphonomethoxypropyl)-8-aza-2,6-diaminopurine.

29. 9-(R)-(2-Phosphonomethoxypropyl)-6-mercaptopurine.

30. 9-(R)-(2-Phosphonomethoxypropyl)-N1,N6-ethenoadenine.

31. A compound selected from the group consisting of 9-(R)-(2-phosphonomethoxypropyl)-2,6-diaminopurine and the 8-aza analog thereof.

32. The compound of claim 2 wherein B is a adenine.

33. The compound of claim 1 wherein B is purine substituted at the 6 position with amino, hydroxy, alkoxy, alkylamino, dialkylamino, aralkylamino, azido, mercapto or alkylthio.

34. The compound of claim 33 wherein the 6 position is substituted with amino or azido.

35. The compound of claim 33 or 34 wherein the 2 position is substituted with amino.

36. The compound of claim 1 wherein is B 8-azapurine substituted at the 6 position by amino, halogen, hydroxy, alkoxy, alkylamino, dialkylamino, aralkylamino, benzoylamino, azido, mercapto or alkylthio.

37. The compound of claim 1 wherein alkyl is methyl or ethyl.

38. The compound of claim 1 wherein B is adenine, 2,6-diaminopurine, 2-aminopurine, hypoxanthine or xanthine or the 8-aza analogs thereof.

39. The compound of claim 1 wherein B is substituted with amino, alkoxy, alkylamino, dialkylamino, aralkylamino, benzoylamino, azido, mercapto or alkylthio, and wherein alkyl independently is C3, C4, C5 or C6 alkyl.

40. The compound of claim 39 wherein alkyl is 2-propyl, n-pentyl or neopentyl.

* * * * *